(12) United States Patent
O'Halloran

(10) Patent No.: US 8,392,244 B1
(45) Date of Patent: Mar. 5, 2013

(54) DIRECT ONSCREEN ADVERTISING OF PHARMACEUTICALS TARGETED BY PATIENT DIAGNOSES WITHIN THE CONFINES OF A MEDICAL RECORDS SOFTWARE SYSTEM

(75) Inventor: Laurence R. O'Halloran, Arlington, VA (US)

(73) Assignee: Laurence R. O'Halloran, Arlington, VA (US)

( * ) Notice: Subject to any disclaimer, the term of this patent is extended or adjusted under 35 U.S.C. 154(b) by 4228 days.

(21) Appl. No.: 10/067,885

(22) Filed: Feb. 8, 2002

(51) Int. Cl.
*G06Q 30/00* (2012.01)
(52) U.S. Cl. .................................... 705/14.1
(58) Field of Classification Search ............ 705/14, 705/2, 3, 14.1
See application file for complete search history.

(56) References Cited

U.S. PATENT DOCUMENTS

| | | | |
|---|---|---|---|
| 5,737,539 A | 4/1998 | Edelson et al. | |
| 5,758,095 A | 5/1998 | Albaum et al. | |
| 5,884,273 A | 3/1999 | Sattizahn et al. | |
| 5,915,243 A | 6/1999 | Smolen | |
| 5,933,811 A | 8/1999 | Angles et al. | |
| 5,950,630 A | 9/1999 | Portwood et al. | |
| 6,000,828 A | 12/1999 | Leet | |
| 6,014,638 A | 1/2000 | Burge et al. | |
| 2002/0035484 A1 * | 3/2002 | McCormick | 705/2 |

OTHER PUBLICATIONS

RxCentric and MedManage Systems Partner to Expand Physician Use of Innovative Online Drug Sampling-Alliance Gives Pharmaceutical Companies Broader Physician Access to Drug Detailing and Sampling Programs, Business Wire, Mar. 20, 2001 (Dialog file 610: 00483951).*
RxCentric and MedManage Systems Partner to Expand Physician Use of Innovative Online Drug Sampling-Alliance Gives Pharmaceutical Companies Broader Physician Access to Drug Detailing and Sampling Programs (Dialog file 610:00483951 ).*
Michael Hardy, Potomac Tech. Journal, Apr. 24, 2000, "Rx for success: online medical record system".

\* cited by examiner

*Primary Examiner* — Daniel Lastra
(74) *Attorney, Agent, or Firm* — Hunton & Williams LLP

(57) ABSTRACT

A method of diagnosis-specific advertisement within a prescription writing software system to enable prescription companies to purchase specific diagnoses for which to have their prescription products advertised.

51 Claims, 14 Drawing Sheets

DIRECT ONSCREEN ADVERTISING OF PHARMACEUTICALS TARGETED BY PATIENT DIAGNOSES WITHIN THE CONFINES OF A MEDICAL RECORDS SOFTWARE SYSTEM

FIELD OF THE INVENTION

The invention relates to a method of diagnosis-specific advertising within a medical records software system and more specifically within a prescription writing software system. Advertising of pharmaceutical products in this system is linked to medical diagnoses for which the product may be utilized. The advertiser such as a pharmaceutical company may purchase specific diagnoses that are related to the pharmaceutical product they wish to promote.

BACKGROUND OF THE INVENTION

Hundreds of millions of dollars are spent each year marketing new and existing drugs to health care providers by pharmaceutical manufacturers and marketing companies. This is a cost of business that draws financial resources away from the vital research and development efforts of developing novel drug products.

Current pharmaceutical marketing efforts involve a variety of modalities. The most traditional and costly is the direct marketing of pharmaceuticals to physicians in their office practices by a huge workforce of pharmaceutical sales representatives known as "drug-detailers". During visits to physician offices, information on new and existing drug products is passed on verbally, with pamphlets and brochures and samples are left for physicians to try-out. Often, it is difficult for the representatives to get the attention of busy physicians and sufficient time is often lacking to inform the physicians about the merits of the various products. In an effort to supplement these efforts, pharmaceutical representatives typically leave note pads, pens and other paraphernalia that have the branded name of the pharmaceutical product embedded thereon so that the physician will be reminded about the availability of that pharmaceutical product. This system has its drawbacks because many times these particular methods of advertising are not available at the time when the physician is ready and willing to try a new medication but the dosing information is not at hand.

Another modality of marketing pharmaceutical products to physicians is via traditional advertisement in trade and specialty journals and magazines. Even if the advertisement in the journal is seen and read and the merits acknowledged, the indication, dosage and other particulars of the drug are often forgotten by the physician when the time comes to actually write the prescription in the busy office environment.

The limitations and restrictions of the above marketing modalities hamper the effective and efficient bringing of new drugs to the market and the continued sale of existing drug products. An object of the present invention is to overcome these and other drawbacks inherent to existing systems.

The ideal method of advertising of pharmaceutical products would involve placement of advertising for a drug product that is pertinent to a patients problem in front on the physician at the time the physician is seeing that patient and deciding upon an appropriate medication. This would ideally involve display of advertising onscreen within a MRSS that is used in the office exam room. The specific advertising to be displayed would be driven by the user's selection of a diagnosis or group of diagnoses for the patient on hand. Therefore, only advertising that is pertinent to the current patient's problem would be displayed onscreen during that patient visit. Such a system would give the advertiser a competitive advantage over other products in the same category.

DEFINITIONS

To assist in understanding the present invention, some terminology is provided.

Computer system: One skilled in the art can appreciate that the system may be Web based or based on a variety of networked topologies such as client-server, wireless, peer-to-peer, local area networks, wide area networks, point-to-point dial up connections etc. The system may be contained within a variety of operating systems and platforms such as Windows and Linux and Macintosh and environments such as handheld computers such as the Palm Pilot, PDA's, cellular phones, pagers, laptops and desktop computers and the like. The client system may comprise any combination of hardware and software that may interact with the server or other computer system.

Health care provider (HCP): is intended to include doctors, nurse practitioners, physician's assistants, optometrists, podiatrists, dentists or other parties having prescribing privileges. Health care is intended to cover the broad context of delivery of medical, dental, chiropractic, podiatric, osteopathic and veterinary care.

Encounter: The health-care related interactions between a physician and patient

Prescription writing: The activity of generating a medication order by a health care provider in the prescription writing module. The generated prescription may be then directly output to a printer for presentation to the patient or the order electronically forwarded to a remote location such as a pharmacy either brick-and-mortar or online.

Medical Records Software System (MRSS): A medical records software system comprises a system that records and documents an encounter between a patient and a HCP Point of care may be used to mean that location where the patient/health care provider interaction occurs such as in the office exam room or at the patients bedside.

Pharmaceutical product or "a prescription": This may involve a medication, treatment or other order by a HCP and may be output directly to a printer for presentation to a patient or electronically transmitted over a network such as the internet to a remote location such as an online or brick and mortar pharmacy for fulfillment. As used herein the term "prescription" is intended to include prescription drugs, devices and other items for which a prescription order is generally required Pharmaceutical company: may comprise the dealer, distributor, sales entity, owner, or other entity responsible for manufacturing or marketing a particular pharmaceutical product or other interested parties Prescription Writing Software System (PWSS): A system for the creation of onscreen medical prescriptions during a patient-physician encounter that may be printed at the point of care or electronically transmitted to a pharmacy via e-mail, internet or other electronic networks (with or without the printing of a point-of-care receipt ticket)

Prescription writing system includes at a minimum a screen for recording the patient's assessment or diagnosis(es) and a screen for the treatment plan. The assessment screen displays lists of possible diagnoses from which the user may choose the patient's diagnosis. One diagnosis may be associated with multiple pharmaceutical options. One pharmaceutical may be associated with multiple diagnoses.

The prescription writing software system may reside as one module within a comprehensive medical records software system or exist as a stand-alone software module with the single purpose of prescription writing alone. The system may be either client based or internet based.

Data provider: Data Provider may be individuals or groups of health-care providers or other health care entities (hospitals, surgicenters etc. . . . ).

SUMMARY OF THE INVENTION

An object of the present invention is to allow advertising of pharmaceutical products to health care providers within a medical records software system. A MRSS may contain a variety of modules for the recording of patient history and physical examination data and for detailing a treatment plan. One component of the treatment plan is the issuing of prescriptions for drug products. Alternatively, a stand-alone PWSS may exist without the associated MRSS. Provision is made for the onscreen display of advertising within such MRSS and/or PWSS.

The target of the advertising is the HCP user of the MRSS and/or PWSS. The HCP is the individual who chooses the medication to be prescribed for the patient once a history and physical and evaluation has been conducted and other data such as laboratory and X-ray results have been reviewed. The HCP chooses prescription medications for the patient based on the patient's diagnosis and their training and experience using specific medications. Introduction of newer and perhaps more appropriate and effective medications to a HCP's armamentarium of medication options is one objective of the current invention.

An advertising system is described whereby pharmaceutical companies can purchase rights to have their products advertised onscreen in strategic positions within the MRSS and PWSS. Further, the display of specific advertising content within the MRSS may be selectively triggered by the users selection of a relevant medical diagnosis.

According to one embodiment, pharmaceutical companies are offered the option to purchase onscreen advertising for their pharmaceuticals in a MRSS or in a PWSS. Pharmaceutical products have specific uses or indications based on the medical diagnosis they are designed to treat. When the HCP user of the system selects a diagnosis(es), this triggers the display of advertising for a product related to that diagnosis or group of diagnoses.

Specifically, according to one embodiment, at the end of a patient visit, the health care provider searches for and selects appropriate patient diagnosis(es) in a diagnosis/diagnosis screen within the prescription writing software system. These diagnoses correlate with ICD-9 (International Classification of Diseases-$9^{th}$ edition) codes which are a national standard for coding of medical diagnoses and are currently used by all third party payors for billing purposes. Anyway, and therefore this step is not any additional step other than those usually employed by a HCP at the end of a patient encounter.

Once the diagnosis(es) have been selected for a particular patient, the user then moves to select prescription(s) for the patient that are appropriate for the diagnosis(es) just made. The selection of pharmaceutical products may be made in the same screen as the diagnosis, or in an adjacent screen or in a separate window. In the preferred embodiment, the user selects the diagnoses on one portion of a tabbed screen named "Assessment" then moves to another tabbed screen named "Plan". The "Plan" screen contains a number of tabbed subsections relating to the HCP's plans for the patient's medical care such as Prescriptions, Labs, Radiology, Studies, Consultations, etc. The prescription section ("RX") displays a customizable/user-modifiable list of medications from which to choose to treat the patient's diagnosis or problem. The user searches for and selects the appropriate medication(s) to be prescribed for this particular patient's diagnosis(es).

The prescription list is retrieved from a prescription drug database that is either resident on the client and updated via a network such as the internet or is located remotely on the internet. In one embodiment, the list box displays the default drug dosages, frequencies and routes of administration and the user only needs to single-click in order to select the default prescription. Provision is made for easy alteration of the default dosage and frequency and routes of administration. In addition, with a single-click the list box can be filled with the user's favorites or the patient's current or prior medications. Therefore, no re-entry of data may be required to issue refills of prior medications, only a single-click on the prescription is required.

The advertising module is responsible for rendering advertisement within the MRSS. The advertising display may reside within or adjacent to the prescription selection screen ("RX"). The advertising module may render an advertisement for a pharmaceutical product using a variety of methods involving prominent display of the name of such product within the MRSS. In the preferred embodiment, a banner advertisement is placed at the bottom of the prescription writing screen to attract the health care provider's attention before selection of a medication. Other means of prominent and strategic display of advertising content would include but not be limited to highlighting as larger text or otherwise visually differentiating the product name in the users drug list. The advertising module tracks the users selection of diagnoses and matches the selected diagnoses with a database of advertising content. The advertising content appropriate to the selected diagnosis is then displayed as an onscreen advertisement as described above. The user therefore experiences an interactive display of onscreen advertising material that is immediate in onset and is targeted specifically to the just selected patient diagnosis.

Such an exquisitely targeted method of onscreen advertisement of pharmaceutical products has a high value attached and can justify payment of premium advertising rates. The potential therein exists for the advertiser to positively influence the HCP's prescribing pattern at the very time the HCP chooses amongst a number of pharmaceutical treatment options.

Advertisers may selectively target practitioners with advertising content stratified by HCP specialty, location and other demographic or other parameters desired for marketing purposes. Advertising content may be changed dynamically by periodic or continuous updates via connection of the users PWSS with the central server system over a network such as the internet. Provision is also made for rotation of advertising content on varying time schedules. The described system provides a superior means of promotion of pharmaceutical products that eliminates the numerous disadvantages of current methodologies.

Information regarding the prescription of such product, including but not limited to dose, frequency, interval, medical indications, contraindications etc are made readily available to the prescribing practitioner as a component of the advertisement so as to encourage use of the product without further research.

Other objects, advantages and benefits of the present invention will be apparent from the description provided below to one skilled in the art.

Advertisers and Sponsors:

Advertising may be purchased on the system by a variety of interested parties. Pharmaceutical companies or their marketing organizations would form the primary group of entities that would have an interest in participating as advertisers. Other interested parties include entities involved in medical and health care activities such as hospitals, laboratories, radiology providers, treatment facilities such as physical therapy facilities, ambulatory surgery centers, managed care plans, HMO's and pharmacies among others. Non-medical entities such as financial services organizations could also be served with targeted advertising to high-net worth physicians Advertising Formats:

Advertisement is displayed in the Graphical User Interface (GUI) within or adjacent to the onscreen area in which the prescription selection and writing occurs. Pharmaceutical advertisement may comprise a variety of formats including banners, buttons, logos and sponsorships and may consist of static, animated or rich media content. A variety of methods of advertising are possible all involving the prominent display and/or visual differentiation of the pharmaceutical product within the MRSS including but not limited to the following.

Sponsorship is the provision for an advertiser to display their advertisement or logo within the MRSS or PWSS such that it is continuously present. This allows for display of advertising during "downtime" when no diagnosis has been selected or when no advertisement is available for the selected diagnosis.

At the conclusion of the patient visit the physician searches for and selects the appropriate patient diagnosis code in the "ASSESSMENT" screen. These codes are currently required by all third party payors for billing purposes. These codes come from a public domain reference list called the ICD-9 (International Classification of Diseases-$9^{th}$ edition) which is the national standard for coding of diagnoses.

Next the user moves to the "PLAN" screen which has a sub-section "RX" for prescriptions [other sections are for other treatment plan options such as x-ray, surgery etc]. This "RX" screen displays a customizable/user-modifiable list of medications in the prescription list-box from which the user may choose. The user searches for and selects the appropriate medications to prescribe for this particular diagnosis. The prescription list-box may take on a variety of formats involving the display of relevant medications and a means for the user to select from amongst the displayed medications. In the preferred embodiment, the prescription list-box is a list box displaying lines of text that describe the medications name, dose, route, frequency, duration, refill availability, substitution permission and other relevant data related to the medication prescription. Adjacent to the text line is a check box that when checked indicates that the medication is to be prescribed.

Once the diagnosis or multiple diagnoses are selected in the software module, the advertising database module is queried to return a banner ad appropriate for the selected diagnosis or diagnoses. The banner ad is then displayed prominently but tastefully adjacent the prescription selection screen of the prescription writing module. Depending on the layout of the MRSS, the prescription selection module may appear only after the diagnosis has been selected in another screen. In any case, the advertising to be displayed is determined by the selection of the patient diagnosis at each individual patient visit. The objective of this design is to positively influence the physician choice of medication that will be selected for the diagnosis just made.

The advertising database module may be resident locally on the client or may reside remotely and be connected via the internet. Advertising database resident on the client may be kept current with periodic automatic internet updates that allow dynamic changes in the advertising content and periodic updating of diagnosis/medications associations.

Indirect Advertising:

Pharmaceutical products may be advertised with indirect techniques not involving the overt display of an advertisement of the drug by modifying the placement of a drug within the prescription list box. A variety of formats exist for the differential display of a pharmaceutical in the prescription list box. These include highlighting the drug in different color, font style, font size, underlining, italicizing, bolding, flashing text or other visual effects. Another technique of differential display involves modifying the positioning of the drug in the list box such as placing the advertised drug product first in order in the list of available options, or may be differentiated using any other method that sets apart the particular prescription from other available prescriptions for the particular diagnosis or group of diagnosis.

Banner Ad Extensions:

In concert with the targeted display of diagnosis relevant pharmaceutical advertising content, another object of the present invention is to provide a PWSS whereby the advertisement component itself contains a series of embedded elements designed to extend the users knowledge and information about the advertised product and enhance the users ability to reach out and gather additional information regarding the product. Provision is made for extensions to the banner advertisement which reside embedded within or alongside the banner ad. Such extensions provide additional functions and allow the user to go beyond the initial advertising display to glean additional information.

Drug Info:

One type of ad extension involves a link that is embedded within the advertisement to allow the user to access more in-depth information on the advertised drug. An advertised drug that is unfamiliar to a HCP is unlikely to be prescribed unless the HCP has detailed knowledge of the products properties. Pertinent properties of a pharmaceutical product may include but not be limited to indications and contra-indications for use, risks, adverse reactions, drug-drug interactions, use in pediatric/nursing and pregnant patient populations, correct dosage ranges, frequency and duration of use, foimulary compliance, cost information such as average wholesale prices and other pertinent details.

In one embodiment, detailed drug information is rapidly accessible onscreen by the HCP through the graphical user interface at the time the prescription is chosen. A panoply of details regarding the advertised product may be readily accessed via embedded components of the advertising module. Such details include but are not limited to insurance formulary coverage, cost information, dose and side-effects.

In the preferred embodiment, the PWSS would provide immediate onscreen access to a drug information system via an interaction with the advertisement. The drug information system would provide the user detailed information regarding the advertised drug of interest. In the preferred embodiment, the user interaction with the advertisement would represent a click on the banner ad itself or a portion of the banner ad or a button or hyperlink adjacent or within the banner ad. Other forms of user interaction are also possible. The drug information system would reside on the client or on a database server on the network such as the interne and as such be readily updatable. In its preferred embodiment the drug data would be encoded in XML format for maximum flexibility of display and manipulation on the client side Auto Add:

Another type of ad extension involves the property of an advertisement that confers the ability of the advertising component to interact with the user's prescription list box. In one embodiment, the user clicks a button or hyperlink on the advertisement to automatically add the advertised drug directly to the users "hot list" of drugs. As such, the drug becomes immediately available in the prescription list box for prescribing. All relevant prescribing information such as available doses and routes of administration for that particular product are also added to the prescription list box's data store. In another embodiment, the advertised drug and its associated information is automatically downloaded into the prescription list box although this automatic feature may be optionally disabled by the end-user.

Placement of a drug in the users list increases the probability that a given drug will be prescribed in the future. The advertising content includes embedded information regarding default and standard doses such that the user can add the default prescribing information to the prescription writing list with minimal effort. The embedded information is contained in XML format as a prescription object.

Communication:

Another type of ad extension allows direct communication and feedback to the pharmaceutical company sponsoring the advertisement. The functionality required to allow rapid communication and feedback to the advertiser is embedded into the advertising module and advertising component. Communication and feedback may take-on a variety of forms and serve a variety of functions not limited to the following. Information regarding the advertised product may be accessed via prompts for live telephonic consultation with a customer service representative, e-mail messaging, instant messaging systems, links to product's companion web sites. Messages may be sent to the advertiser requesting further information regarding the product. Messages may be sent requesting that the advertiser provide samples of the product or to have a representative visit the office. Single click on a "samples" button automatically transmits request for samples to appropriate entity via e-mail or other TCP/IP messaging system. User identification such as name, address etc is automatically drawn from the module's provider registration database. Messages regarding clinical outcomes of the drug may be sent to the advertiser to provide direct and timely data on the clinical efficacy of the product. Data of interest include such information as response of patient symptoms to drug administration and adverse drug effects. In its mature state, this system forms the basis of a productive feedback loop between the drug company and physicians.

The advertisement may also comprise recruitment pitches to participate in clinical studies that may or not be specifically related to the assigned diagnosis or prescription. In one embodiment, physicians are selectively recruited for clinical studies after selecting diagnoses of interest to the clinical study group. The provides an exquisite selectivity in recruitment based on diagnoses. Physicians are rewarded for their participation in clinical studies using a point rewards system similar to frequent flyer miles.

Revenue Generation/Compensation:

The present invention provides an opportunity for revenue generation by the advertising system that acts as the distributor of advertising content. A system of revenue generation and compensation is described for onscreen pharmaceutical advertising placement within a MRSS involving an advertising system and advertisers. In one embodiment, the advertiser places advertisements in the advertising system and the advertiser compensates the advertising manager for provision of targeted advertising services. The advertiser purchases rights to individual or multiple related or unrelated diagnosis codes. These diagnoses are most easily specified using the health care industry standard diagnosis codes (ICD-9, ICD-10). This takes advantage of the fact that each and every patient encounter requires the selection of a diagnosis code or codes in order for insurance claims to be paid. Therefore, the selection of diagnosis codes by the user is a step that is a required and normal step by the user in the usual workflow sequence. The purchase of a diagnosis or group of diagnoses would confer on the purchaser an exclusive or preferential right to advertise or otherwise display their product within the MRSS and PWSS every time the diagnosis or group of diagnoses are selected by the system user. In common parlance, this would be known as "buying a diagnosis". The level of compensation is related to the number of diagnoses purchased and their relative frequency of occurrence in medical practice and other parameters based on marketing experience.

The advertiser may wish to purchase multiple diagnoses for a single pharmaceutical product since a single medication may have multiple indications or diagnoses for use. An example is a new antibiotic which is indicated for treatment of both sinus infections and ear infections.

Advertisers may also wish to purchase specific combinations of diagnoses that when selected together rather than alone will trigger the appearance of an advertisement. A particular combination of diagnoses may suggest a drug to use that would not be indicated for either diagnosis alone. An example is the new class of anti-inflammatory drugs that are indicated for arthritis patients with gastric ulcers who cannot tolerate traditional anti-inflammatory drugs such as Motrin. The drug Celebrex™ is one such drug. In this case, if the diagnoses arthritis and gastric ulcers were selected or already existed in the record of a patient, then a display ad for Celebrex™ would appear. This system also has the ability to interact with the patient's stored clinical data describing prior visits and diagnoses.

Although a single diagnosis may be purchased by one pharmaceutical company, that same diagnosis, when combined with another diagnosis, may be sold to a different pharmaceutical company. For example, Zomig™ is a medication for the treatment of migraine headaches. Whereas the migraine headache diagnosis may have been purchased by Zomig™, the combination of migraine headaches and Alzheimer's disease may be purchased by another pharmaceutical company that wishes to market a new drug which has beneficial affects for Alzhimer patients suffering from migraine headaches.

The advertiser may selectively target practitioners by specialty, location, practice parameters and other demographic or other parameters desired for marketing purposes. The HCP user demographic profile is created with initial registration and transmitted back to the central system. An advertiser may wish to target their ads to a specific sub-group of physicians. For example, advertising for a new generation anti-histamine could be targeted only to ear nose and throat specialists and allergists.

In another embodiment, the same diagnosis could be purchased by multiple advertisers but the advertising system would place different advertising content onscreen depending on user demographic data. For instance, two competing migraine headache products could be targeted to different physician groups. The older more established product could be targeted to the family practice physicians whereas a newer more sophisticated medication could be targeted to neurologists who typically treat more difficult cases and would be more likely to use the newer drug.

In another embodiment, multiple advertisements for the same diagnosis may be rotated on varying time schedules.

According to another embodiment of the present invention, multiple advertisers may purchase rights to the same diagnosis but based on their level of subscription have stratified rights to display their advertisement. In this embodiment, different levels of prominent display may be offered to different participants based on their level of subscription. For example, a platinum membership, gold membership and silver membership may each be sold for a single diagnosis or combination of diagnoses. As in FIG. 6a below, for example, Zomig™ may purchase the platinum membership for the diagnosis "migraine headache" entitling it to a prominent banner display advertisement. The drug Cafergot™ may purchase the gold level for the same diagnosis entitling it to automatically appear emboldened in the prescription writing list box. The drug Maxalt™ may purchase the silver level membership and be entitled to automatic italicizing in the list box. Other combinations and permutations of this concept are possible involving differential display of advertising based on levels of membership in the prescription advertising system. For instance, banner ads may be rotated on varying time schedules such that the platinum level ad is displayed 60% of the time, the gold level ad is displayed 30% of the time and the silver level ad is displayed 10% of the time. In another example, three separate banner advertisements may be provided with different sizes corresponding to the platinum, gold, and silver membership. Also, the order of presentation may be by order of platinum, gold, and silver, with decreasing size of font and highlighting.

Some drugs would be hard to target to specific diagnoses such as a new pain to medication which may be useful in a broad range of diagnoses. Advertising however in this cases could be accomplished in a random fashion by intermingling these ads amongst the targeted ads and by cycling the ads.

Tracking:

Provision is made for the system to track user interaction with the advertising component and the prescription list box and its extensions. The collected data is transmitted back to the central system for analysis.

Data of interest includes user interactions with the advertising component and extensions and/or prescription list boxes. For example, click-through rates on advertisements may be followed. Other parameters recorded include but are not limited to, whether a prescription is written for the advertised product, whether the advertised product is added to the user's "Favorites" list. Such response tracking has valuable potential for marketing purposes.

Data Collection:

An additional methodology may be provided by the present invention to facilitate the collection and analysis of clinical data. In a system of the present invention, the central system aggregates information received from a plurality of health-care providers and provides such information to other entities for compensation. These entities may include pharmaceutical manufacturers, distributors and pharmaceutical marketing and research companies. This system provides also for revenue sharing or compensation of the data provider. The system collects medical and healthcare data from a plurality of providers to a central system over a network such as the internet to a central system or via a peer-to-peer network. The central system then serves as a collection point for the plurality of medical and healthcare data that may be aggregated, filtered and analyzed to create a valuable data source of clinical knowledge. This data source may then be provided to interested parties such as research institutions, universities, pharmaceutical companies and market research companies for commercial and academic analysis. Standard data mining techniques may then be applied to the accumulated warehouse of data. The individual data provider, such as the physician user of the medical records software system, is incentivized to provide data to the system by a compensation system such as a point reward system. The data of interest to be provided includes all forms of patient and other clinical and demographic data such as but not limited to prescription information, medical outcomes data, diagnoses, and billing information.

Background Related to Data Collection

Pharmaceutical companies have a great need for accurate information on how their pharmaceutical products are being prescribed and utilized. Detailed information on which physicians are prescribing their and their competitor's products and the frequency of the prescription and the diagnosis for which the product is prescribed are very useful for marketing purposes.

Pharmaceutical companies are at a disadvantage under existing systems because it is difficult for them to gather accurate information on physician prescribing patterns. This data is currently obtained by purchasing data from pharmacies and by polling physicians who may or may not be willing or have the time to provide this information. One of the limitations of acquiring data from pharmacies is that no diagnosis information is recorded when the prescription is filled. In other words, the pharmacies are able to provide information on drugs prescribed but they are unable to provide the diagnosis for which a given drug was prescribed. Therefore, the marketing company has no way of knowing whether the antibiotic Ceftin is being used to treat pneumonia in children or sinusitis in adults. Further only a minority of pharmacies participate is such data collection schemes leaving the data incomplete and biased towards only pharmacies participating in such schemes. Many smaller independent pharmacies do not participate, and these may have important statistical and demographic variances from the other pharmacies thereby skewing the data. For instance, the smaller, "mom-and-pop" pharmacy may be more likely to cater to a greater degree to elderly patients than the larger chain-type pharmacy. The collection of prescribing data is logically best accomplished at the source of the prescription which is the physicians office. The limitation of this approach is that in order to have meaningful data, a large enough sample size of participating physicians is required.

Another method provided by the present invention proposes a system to collect clinical and drug prescribing data directly from the physician source by accessing the data directly from the physician's Medical Records Software System (MRSS) and Prescription Writing Software System (PWSS) which includes both prescription information and associated diagnoses.

Data may be attached to demographic data and medical data such as diagnosis and if a follow up visit to outcomes information. This clinical data from a plurality of health care providers may then be uploaded and collected in a central system where traditional data mining techniques are applied to the aggregated data. Information is assembled and aggregated in either raw or refined form for later analysis, determination of trends demographic relationships and data mining.

Compensation:

It is another object of the present invention to provide a system whereby health care data providers are compensated for information provided to the system. Revenue generated from distribution of this information may be shared and distributed between the health care providers, the prescription issuing system distributors, the central system, agents for the central system, data analysis entities, and pharmaceutical companies as the various entities determine to be appropriate. The source of the data, the health care provider using the MRSS is encouraged to participate in information sharing with an incentive system. The individual health care provider's data is not very valuable in isolation but aggregated with multiple other sources it becomes very valuable. The data provider may be compensated on a variety of parameters including but limited to data volume and data quality. Clinical data is of variable value and therefore has variable "point-value" based on its relative value. Data which has been excessively scrubbed of demographic information would for example be considered less valuable and thereby generate a lower level of compensation. Various types of compensation may be provided and should not be limited hereby. In one embodiment, the data provider may be compensated with reward points based on the amount and quality of data uploaded. This system would be analogous to the airlines frequent flyer mileage program. Data provider rewards are based on points accumulated in account and may be granted as cash payments, discount from software costs, frequent flyer miles, gifts from a catalog or other forms of revenue sharing or compensation. One other form of compensation is the provision of feedback to the data provider in the form of information of comparative nature that shows that provider's data versus normative data for other providers. Other embodiments may also be provided to create incentives for the health care provider to automatically upload data to the central system.

Deidentification/Anonymization:

All health care data carries with it great privacy concerns for both the patient and the physician data provider. An important object of the invention is the provision of a system within a health-care providers medical records software system for de-identifying or anonymizing confidential medical data prior to transmission over the internet to the central system. Option for varying levels of data de-identification, for instance only patient age could be provided in order to protect date of birth information transmission and zip code alone could be provided to limit the amount of geographic information uploaded.

According to one embodiment of the present invention, a module may be provided for the Medical Records Software System that takes the confidential medical data in the database and screens out all patient identifying information to make the information anonymous. Further, the module may allow the healthcare provider to screen data prior to transmission to the central system to give the provider control over what types of data are being provided to protect the privacy of the patients and to limit the scope and type of data provided. An onscreen data review process is provided to allow the provider to review every piece of data or the data in aggregate before it is transmitted. It is also possible that the only data transmitted to the central system is aggregated data from all of the providers patients which helps to alleviate confidentiality concerns with itemized data. Encryption and authentication of data using digital certificates and signatures may be provided to protect the privacy of the data.

Periodic Collection of Data:

Provision of a system is which data is periodically collected from a plurality of medical records software systems via the internet to a central system for analysis and data mining.

Data Type Collected:

One embodiment represents the collection of data from a plurality of health-care providers. Types of data collected (includes but not limited to) may take on many forms. The information recorded for uploading may comprise any data collected in the medical record software system and/or prescription writing system.

Data includes all aspects recorded in a patient-physician encounter such as history of present illness, past medical history, past surgical history, medication history, allergy history, social history, family history, review of systems, physical examination, laboratory results, radiological studies, prior treatments and physician evaluations. Data also includes data captured in follow-up visits which provide temporal information and outcome results of treatment Typical data include provider data such as provider name, specialty, location, zip and practice information as well as provisions for multiple associate providers in group practices; billing data such as all information contained on a HCFA-1500 claims forms including diagnoses and procedure codes, date-of birth, zip code, insurance companies except patient identifying data according to one embodiment of the present invention. Pharmaceutical prescribing data is a key focus and includes all data contained in written prescriptions. The prescription data may or may not be provided with linked diagnosis codes. Another collected data type is clinical outcomes data that represent patient responses to treatments which may include prescription drug treatments. Outcomes data is collected over a series of patient visits and represents the change in data parameters such as patient symptoms over time and in response to various applied treatments. In the case of drug treatments, drug compliance, side-effects and efficacy data are recorded on the patient's follow-up visit. Efficacy is determined by evaluating changes in a patient's symptom set in response to a treatment intervention which may or may not include prescription drug treatment. For example, a cough could be unchanged, improved, worsened or resolved from the prior visit in response to the administration of the antibiotic Amoxicillin.

| PARAMETER | RESPONSE | INTERVENTION |
|---|---|---|
| Cough | Resolved | Amoxicillin |
| Headache | Improved-Markedly | Ice Pack |
| Fever | Resolved | NONE |
| Nausea | Worsened | Compazine |
| Vomiting | No Change | Liquid Diet |

Coupons:

An additional methodology may be provided by the present invention is an extension of the PWSS to allow the printing of coupons at the point-of-care simultaneous with the printing of patient prescriptions. The specific coupons printed are determined by factors including the patient's diagnoses and the prescriptions issued to the patient.

As part of the printing process, coupons may be presented to the patient along with the prescription being printed. The determination of what coupons are printed may be driven by a variety of factors including patient demographics, patient insurance, patient medications and prescriptions and patient diagnoses.

Particularly, a coupon module may be provided that interacts with the prescription writing software system to determine coupons that might be of interest to the patient or to the coupon issuer based on these factors.

For example, a particular pharmacy may be interested in acquiring patients with a particular health insurance due to improved reimbursement from that insurance plan. Or a pharmacy may wish to acquire patients in a particular age group to allow improved cross-selling of pharmacy products. For example, a particular type of antihistamine may be provided with a rebate to entice the patient to fill the prescription with that particular brand as opposed to a generic.

The coupon may be printed as a separate paper slip or printed as part of a prescription receipt with a tear-off connection. The coupon may be attached or unattached to the prescription or the prescription receipt.

The coupon is more likely to be used since it is issued at the point of service and handed out along with prescription slips. Typically, patients leave the provider's office and go directly to the pharmacy with the prescription in hand. With this structure, the patient is more likely to redeem that coupon and therefore the coupon issuer is more likely to receive the benefit it seeks through issuing the coupon.

The coupon database may be updated along with the prescription system. The coupon list may be maintained in the MRSS and accessed when prescriptions are written. When a prescription is printed, the database is screened for associated coupons. If an appropriate coupon is available for a particular drug, then the coupon is printed along with the prescription slips or prescription receipts. As part of the system, a coupon database is provided that is periodically updated with information from coupon issuers. The coupon database contains a catalog of available coupons along with matching parameters of interest for marketing purposes and tables relating to demographic and medical characteristics of target patient groups.

Coupon services may be utilized by a variety of entities. Pharmaceutical manufacturers may use the coupon services to encourage patient refills of their brand of medications. Rebates or discounts may be offered for refills of a medication to encourage patient loyalty. Pharmacies may encourage filling of prescriptions at their stores by offering discounts, rebates or other incentives for patients.

In its preferred embodiment system printer may take the form of a thermal line printer with 4 inch wide continuous roll paper tape. (similar to grocery store checkout printers). Thermal paper may be customized with a logo on reverse to discourage counterfeiting.

Bar Codes:

Once a prescription is transmitted electronically to the pharmacy a prescription receipt is printed for the patient at the point-of-service containing a bar code imprint that encodes a unique prescription ID generated by the prescription writing software. This unique prescription ID is electronically transmitted encoded with the prescription data. When the patient arrives at the pharmacy, the prescription receipt is scanned by a bar code reader for easy match-up and authentication with the electronically transmitted prescription data.

BRIEF DESCRIPTION OF THE DRAWINGS

FIG. 3b—Depicts an overview of an MRSS interface according to an embodiment of the present invention.

FIG. 12—Depicts an example of a bar-coded prescription issued by the PWSS according to an embodiment of the present invention.

DETAILED DESCRIPTION OF THE INVENTION

The present invention provides a system and method for enabling pharmaceutical companies to place onscreen advertising within a prescription writing software system that is uniquely targeted to the user based on the diagnosis of the patient that the user is currently attending to. The onscreen display of diagnosis-relevant advertising is triggered by the user's selection of a diagnosis for which the prescription product may be used. The advertising content is therefore linked to and triggered by the users selection of a particular relevant diagnosis or group of diagnoses. According to one embodiment of the present invention, a prescription writing software system in provided within a medical records software system which the health care provider uses to enter the patient's diagnoses and select appropriate prescriptions for that condition. A list of possible diagnoses is displayed and a list of available prescription medications is displayed. After determining the patients diagnosis based on history and examination, the user selects appropriate medications to treat the diagnosed condition. Pharmaceutical companies may purchase rights to display advertising for their product onscreen in the prescription writing area of the system. The pharmaceutical company may purchase rights to specific diagnoses or groups of diagnoses.

According to the present invention, within the software system, a particular prescription may be given preferential treatment through a banner advertisement or other method of highlighting a particular drug when a particular diagnosis has been selected by the health care provider. The operator or distributor of the prescription writing software system may charge or otherwise receive compensation from the drug company for the prominent display of that drug company's prescribed drug.

Figure 1:
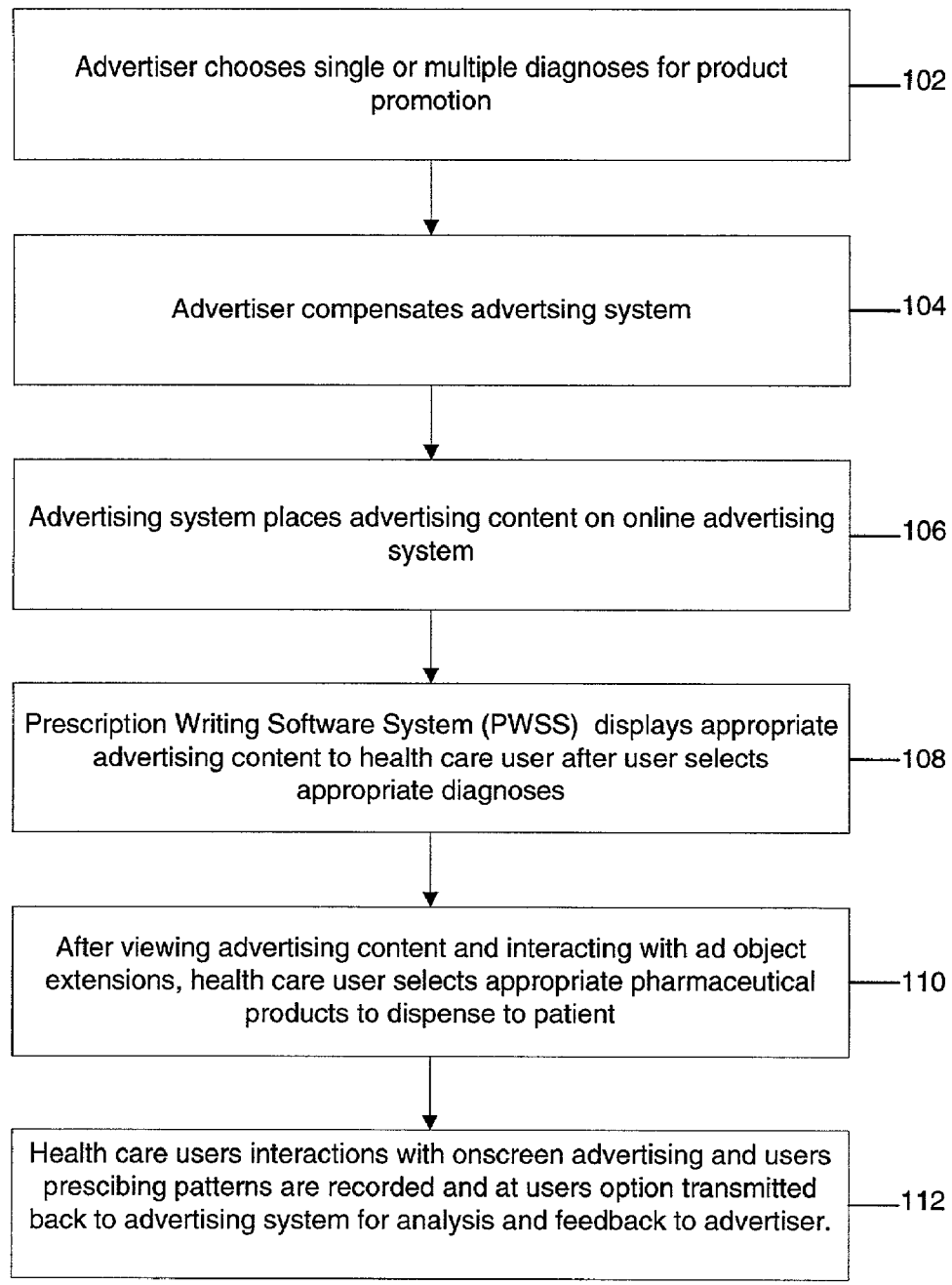
FIG. 1—Depicts the operation of a prescription advertising system according to an embodiment of the present invention.

FIG. 1—Advertising System

FIG. 1 depicts a method 100 according to the present invention. FIG. 1 depicts a methodology according to the present invention by which a particular prescription is prominently displayed or advertised within a prescription writing system of the present invention. It describes an advertising placement mechanism.

In step 102, the advertiser chooses a diagnosis or multiple diagnoses of interests for product promotion. The prescription system assigns the particular diagnosis or collection of diagnosis to a particular prescription advertiser for promotion of that advertiser's diagnosis-appropriate prescription. For example, if the diagnosis of interest is migraine headaches, then the promoter of the drug Zomig™ (a migraine medication) may wish to have that drug be assigned to that particular diagnosis.

Next, in step 104, the advertiser compensates the advertising system. The prescription advertiser compensates the medical record software system distributor, owner or other entity that distributes the prescription writing software, the providers, a network of providers that purchase and operate the prescription writing software, or any other entity having control over the content of the prescription writing software system.

In step 106, the advertising system places the advertising content on its online system connected to a plurality of healthcare provider users.

Next, in step 108, the advertising content is displayed to healthcare provider users in the process of their interaction with the advertising object. A variety of advertising objects are available through the online system for display to the healthcare provider user.

In step 110, the user's interactions with the advertising objects are recorded and transmitted back to the central system for analysis. These user interactions may represent user clicking on the advertising object or the advertising extensions such as auto-add or the clicking of hyper-links for additional information.

In step 112, the central system collects and analyzes the user data, which is then used to enhance the advertising process and is provided to advertisers for marketing purposes.

In other words, according to one method of the present invention, advertising is sold to interested pharmaceutical companies to be displayed in a MRSS and in particular in the PWSS module of the MRSS. In the preferred embodiment, advertising is displayed in the PWSS adjacent to or within the window in which the prescription selections are made. The advertising copy displayed is determined or driven by the users selection of the diagnosis(es) of the patient at hand. Purchasers of advertising services may purchase rights to one or more medical diagnoses such that when the given diagnosis is selected for an individual patient, the purchasers advertising copy is displayed. This creates a unique linkage between the selection of patient diagnoses and the display of advertising that is pertinent to the patient's diagnoses.

Figure 2:
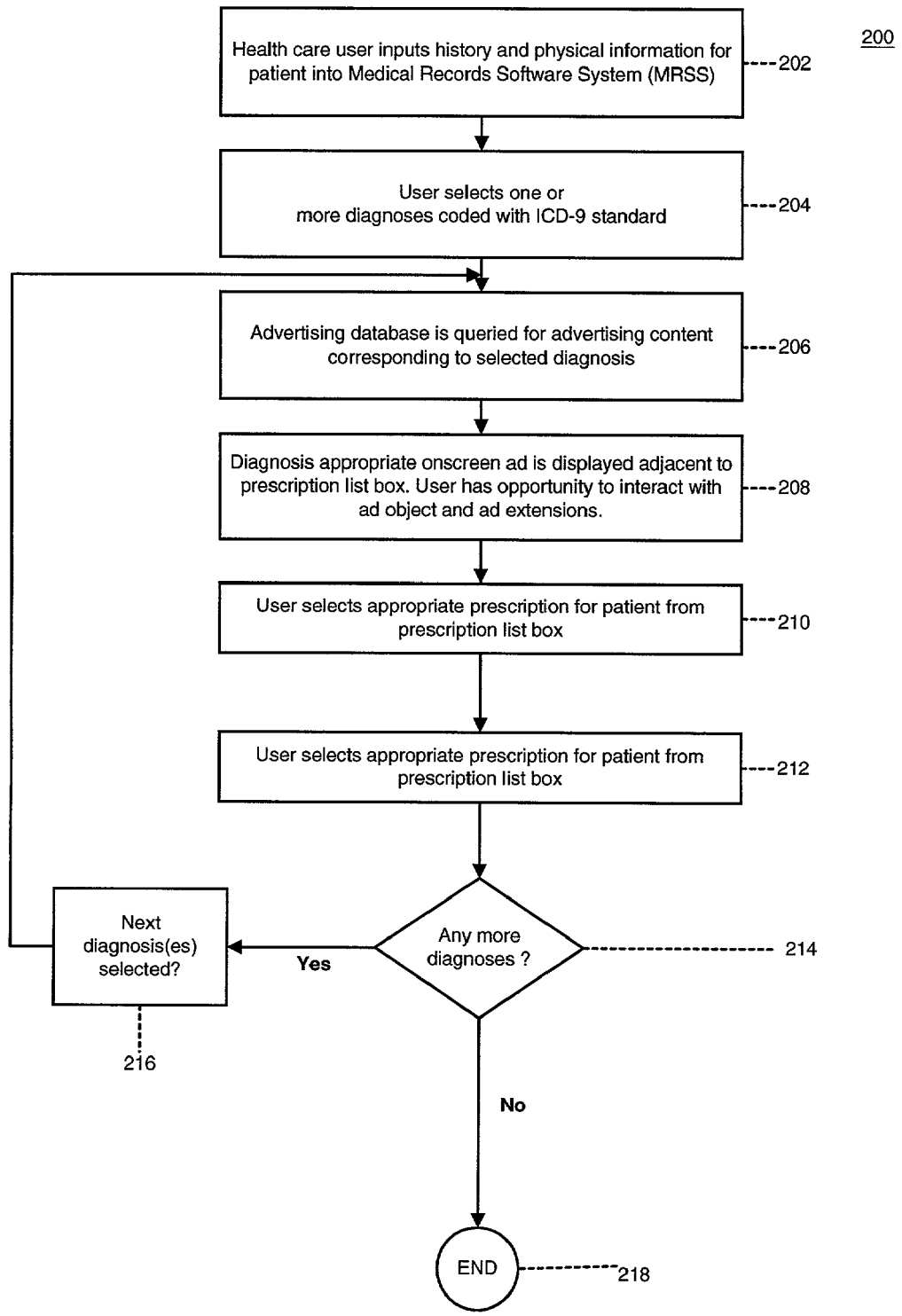
FIG. 2—Depicts the triggering of advertisements based on selection of linked diagnoses according to an embodiment of the present invention.

FIG. 2—Diagnosis Triggering of Advertising Display

FIG. 2 depicts a method 200 according to the present invention. FIG. 2 is a flow diagram that depicts the series of steps that occur in order to trigger the display of an advertising object. In step 202, the healthcare provider user inputs patient history and examination and other relevant clinical data from the encounter into the medical record software system. In step 204, the user selects one or more diagnoses codes that apply to the patient's current encounter at the end of the visit. In step 206, the advertising database in the advertising module is queried for advertising content that corresponds to the selected diagnosis. This process occurs in real time and in an interactive fashion. In step 208, an on-screen ad is displayed adjacent to the prescription list box in response to the user's selection of a diagnosis code. The onscreen ad is displayed immediately after the diagnosis code is selected and there is little, if any, delay in this process. In step 210, the user selects an appropriate prescription medication for the patients from the onscreen prescription list box. It is one object of the present invention that the user's choice and selection of prescriptions may be influenced by the display of the on-screen ad adjacent to the prescription selection box. In step 212, the user's interaction with the advertising object and the prescription list box are recorded and transmitted to the central server for data analysis. In step 214, if there are further diagnoses, then the user proceeds to step 216, in which further diagnoses are selected and the process recurs, if not, in step 218 the process is terminated and the patient is issued their prescriptions either electronically or on paper. The prescription list box is the preferred embodiment of a prescription writing screen, although other means of displaying and selecting prescription products are not excluded. Other formats of display may be entertained.

Figure 3:
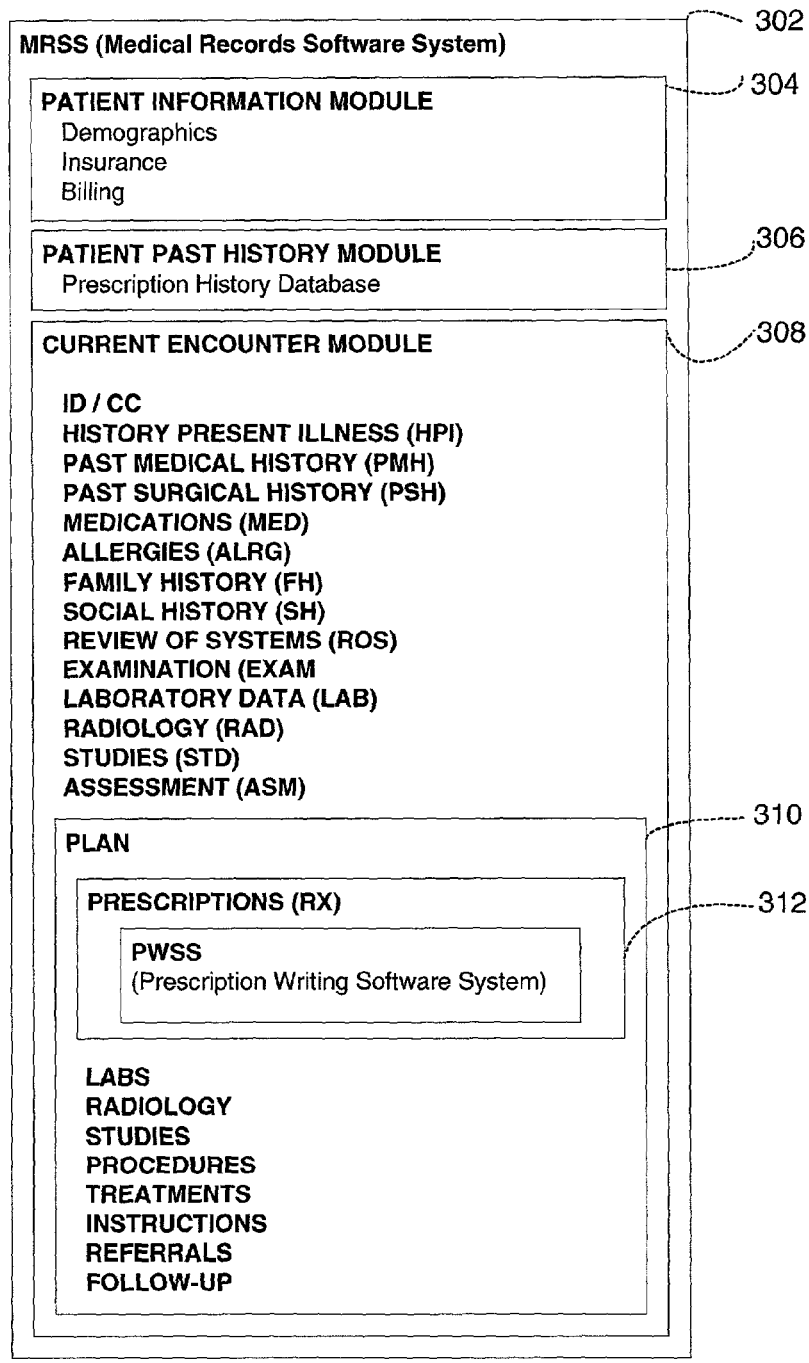
FIG. 3—Depicts a Schematic of a Medical Records Software System (MRSS) and Prescription Writing Software System (PWSS) according to an embodiment of the present invention.

FIG. 3—Schematic of Medical Records Software System (MRSS) and Prescription Writing Software System (PWSS)

FIG. 3 depicts a method 300 according to the present invention. FIG. 3 displays a schematic of a medical record software system and a prescription writing software system. This outline of a medical record software system is provided in order to better describe the organization, structure and placement of the prescription writing software system.

The prescription writing software system may reside within the general medical record software system or may reside as an independent freestanding component. The prescription writing system may be connected to one or more database systems and one or more prescription output devices. Component 302 represents the generic all encompassing medical record software system, which contains component 304, 306 and 308. Component 304 represents patient information module, which handles information such as patient demographics, patient insurance, and patient billing information, which changes little between visits and is therefore fairly static. Component 306 is similar to component 308 in its subsections, but it contains the patient's prior medical history whereas component 308 is devoted to handling the patient's current encounter information. Of specific importance to this invention, component 306 contains the data of the patient's prescription history, which is accessed during current and future visits. Component 308 represents the data being recorded in the patient's current encounter and is broken into traditional history and physical subsections including ID and chief complaint, history of present illness (HPI), past medical history (PMH), past surgical history (PSH), medications (MED), allergies (ALRG), family history (FH), social history (SH), review of systems (ROS), examination (EXAM), laboratory (LAB), radiology (RAD), studies (STD), assessment (ASM) and plan. These sections represent the time-honored traditional breakdown of a patient evaluation in standard medical practice.

The HPI (History of Present Illness) module records standard interview information such as how the patient is feeling, the symptoms the patient describes, or other information that a health care provider normally writes down during the interview of the patient regarding the reason for their visit to the health care provider's office.

The PMH (Past Medical History) module collects past medical history information about the patient including the major illnesses or conditions from which the patient has suffered throughout his or her life.

The PSH (Past Surgical History) module collects information about the patient's surgical history, including the various surgeries that have been performed on that patient. This module also automatically updates the surgical history list when a surgery is performed and prescribed through the PROC tab in the PLAN section.

The MEDS (Medication History) module collects information regarding the various medications that the patient is currently taking and/or has taken in the past.

The ALRG (Allergy History) module collects information about the particular allergies to which the patient is susceptible and provides that information to diagnosis and planning module so the health care provider avoids prescribing drugs that may precipitate allergies.

The FH (Family History) module collects information about the patient's family history, such as major heart disease or other conditions that tend to be hereditary.

The SH (Social History) module collects information related to the patient's social history (e.g., habits such as smoking, drinking, drug use, lifestyle, stress, etc.).

The ROS (Review of Systems) module collects information about the complete system overview of the patient during that particular visit. In particular, even if the patient is complaining about upper respiratory problems, the health care provider typically will investigate all of the patient's major systems to ensure that there are no other contributing factors.

The EXAM (Examination Findings) module collects information about the patients current physical examination findings.

The LAB (Laboratory Data) module comprises an area in which the health care provider may input information about various laboratory and test results from prior and existing conditions.

The RAD (Radiology Data) module enables the health care provider to input information about various radiological procedures performed on the patient.

The STD (Study History) module enables the health care provider to input information corresponding to studies performed on the patient which may be relevant.

The ASM (Assessment) module allows the user to enter diagnoses for the patient to summarize the clinical history and examination. This module presents diagnosis options and records the physician's selections of diagnoses. The diagnoses available to be selected may comprise those from the diagnosis codes available in public domain lists, including the International Classification of Diseases-Ninth Edition (ICDN-9) and SNOMED.

The PLAN section 310 is highlighted for special interest and contains component 312, the prescription writing software system (PWSS). Other components include components for ordering of laboratory tests, radiology studies, other studies, procedures, treatments, instructions, referrals to other physicians and healthcare providers, and a section for ordering and scheduling future patient follow-up visits.

Figure 3B:
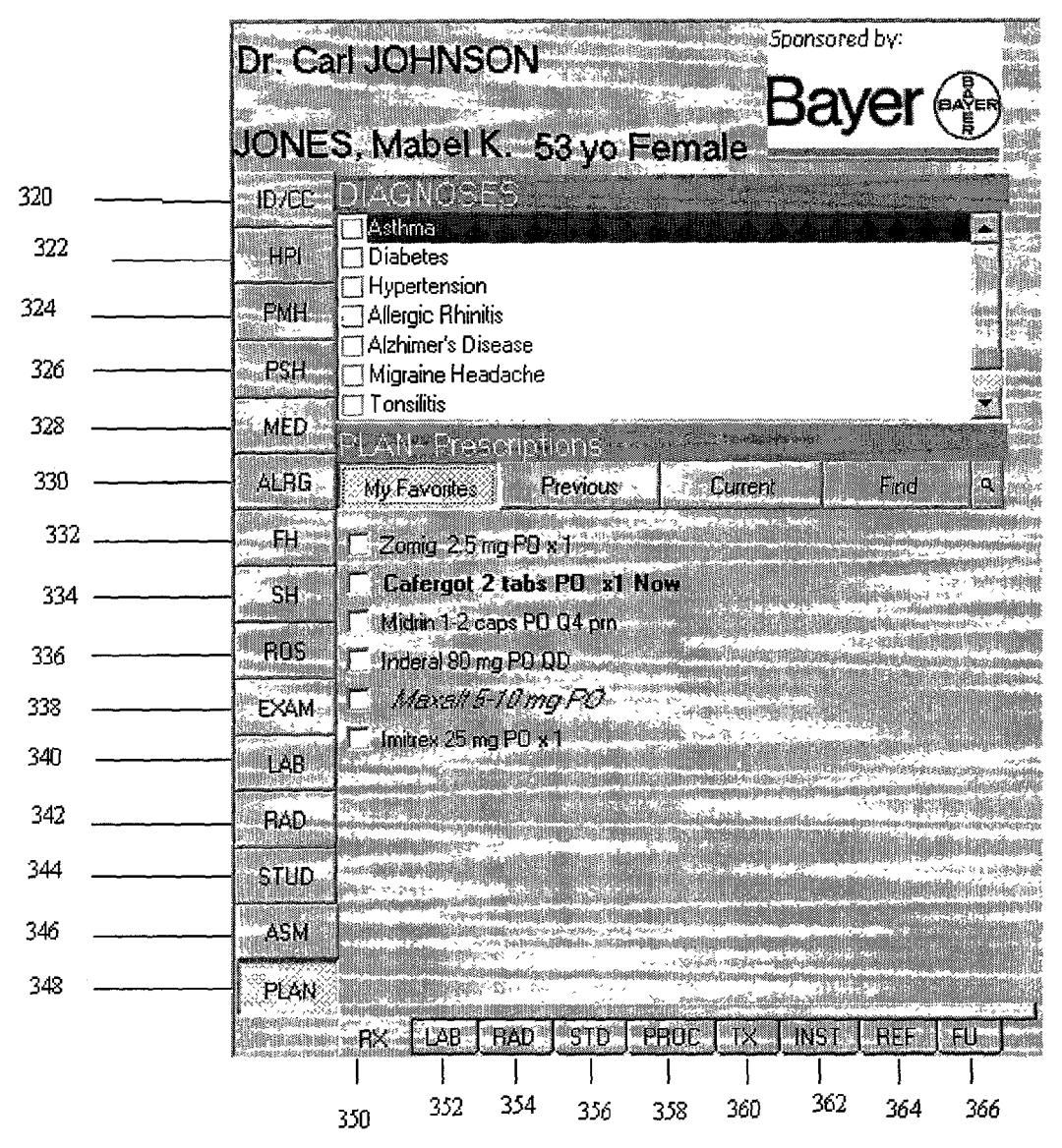

FIG. 3b—Screen Shot of MRSS

FIG. 3b depicts a graphical user interface 300 presented by a MRSS. In particular, a plurality of buttons or selectable icons may be presented within a screen portion as shown. The buttons may correspond to many of the modules depicted in MRSS Schematic FIG. 3. For example, an ID/CC module may correspond with ID/CC button 320 and HPI module may be accessed by HPI button 322. Correspondingly, the medical history module may correspond to PMH button 324, the past surgical history module may correspond to PSH button 326, medication history module may correspond to MED button 328, allergy history module may correspond to ALRG button 330, family history module may correspond to FH button 332, surgical history module may correspond to SH button 334, review of systems module may correspond to ROS button 336, examination module may correspond to EXAM button 338, laboratory data module may correspond to LAB button 340, radiology data module may correspond to RAD button 342, study history module may correspond to STUD button 344, assessment module may correspond to ASM button 346, and plan module 310 may correspond to PLAN button 348.

Within the graphical user interface presented by the plan module, a plurality of other tabs may be presented to record additional treatment plans for the patient in addition to ordering prescription medications.

The RX tab 350 presents a graphical user interface containing a prescription list box that enables the health care provider to choose prescriptions for particular diagnoses. The LAB Tab 352 enables the health care provider to order laboratory tests. The RAD tab 354 enables the health care provider to order various radiological tests, including X-Rays, CAT scans, etc. The STD tab 356 enables the health care provider to order various studies for the patient. The PROC tab 358 enables the health care provider to order and schedule particular diagnostic and surgical procedures for the patient. The TX tab 360 enables the health care provider to choose various non-medication treatments to be prescribed. The INST tab 362 enables the health care provider to create specific and specialized instructions for the particular patient. The REF tab 364 allows the health care provider to enter referral information for the patient to visit other practitioners. The FU tab 366 enables the health care provider to input information regarding recommended follow-up visits for the patient.

Within the prescription writing section a variety of buttons exist to allow the user to locate medications to prescribe. A My Favorites button is provided which causes the display of the users default or favorite medications in the prescription list box. The Previous button causes the display of the patient's prior medications which can easily be re-selected for refill or renewal of medication. A Current button causes the display of the medications that the patient is actively taking. A Find button causes the display of a search screen to allow the user to rapidly find other medications to prescribe from the prescription drug database.

Figure 4:
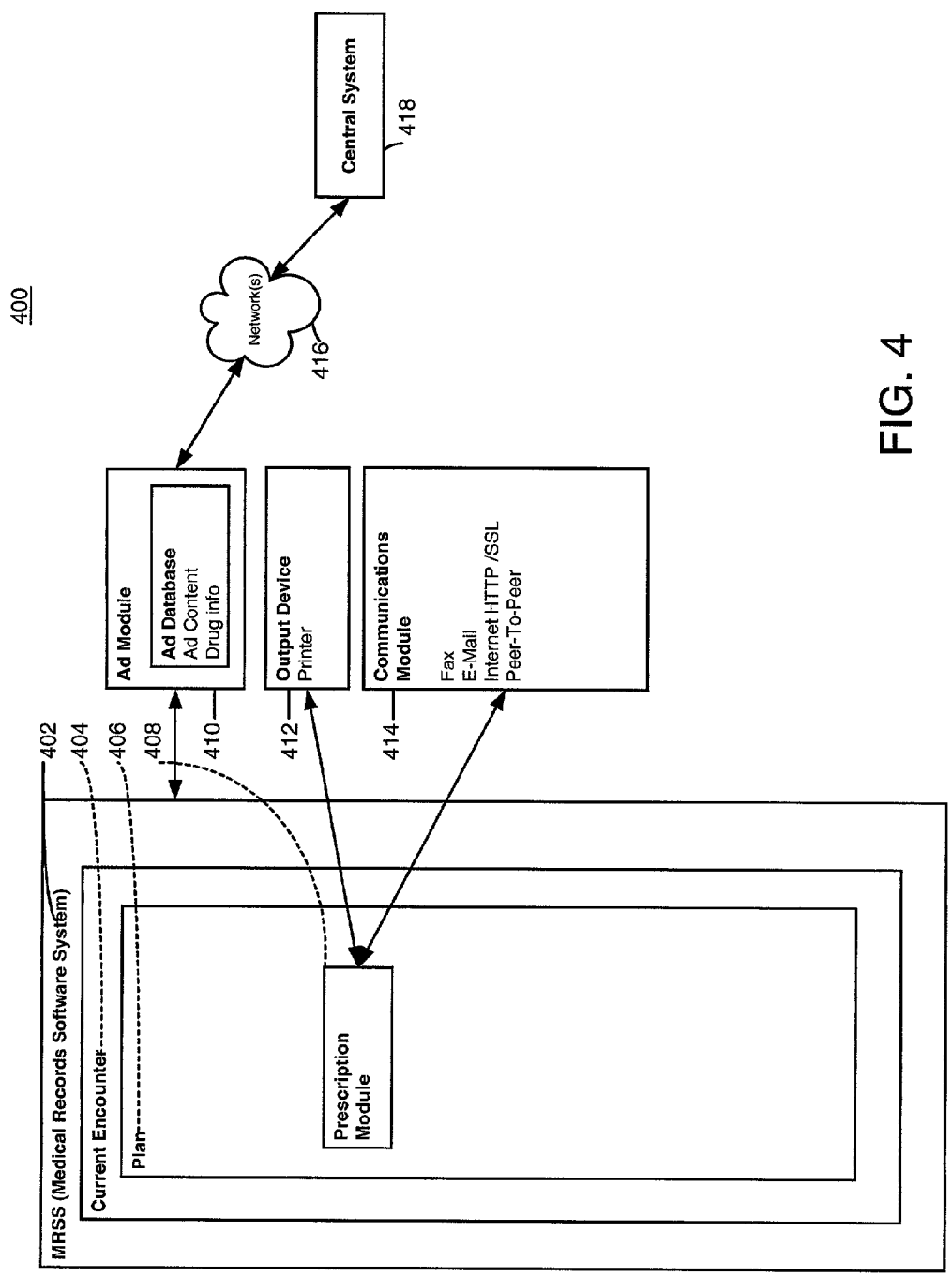
FIG. 4—Depicts the operation of an Advertising System network according to an embodiment of the present invention.

FIG. 4—Advertising System

FIG. 4 depicts a method 400 according to the present invention. FIG. 4 describes the advertising system as it relates to the general medical record software system. Component 402 represents a generic medical record software system. Component 404 represents the current encounter component of the medical record software system. Component 406 represents the plan component of the current encounter component. Component 408 represents the prescription writing software system as integrated component of the medical record software system. Component 410 represents the advertising module, which contains among other components an advertising database, which contains among other data an advertising content database and a drug information database. Component 412 represents an output device, the preferred embodiment of which is a printer. The preferred embodiment of the printer represents a thermal line printer similar to that which is seen at a grocery checkout counter with auto-cut feature for separating individual prescriptions, printing coupons, and other relevant order forms and order slips necessary for the routine transaction of medical care. Component 414 represents the communication module, which handles communication between the medical record software system and outside systems. The communication module handles Internet connections via HTTP/SSL, e-mail, fax, peer-to-peer and a variety of other communication methodologies. Component 416 represents the network, the preferred embodiment of which is the Internet. Component 418 represents the central system through which the advertising system is controlled and updated.

Interactions between component 408 and prescription writing software system include a two-way interaction between the prescription writing software system and advertising module component 410. Once the user has selected a diagnosis within the medical record software system, this triggers the display of advertising content within the medical software system. The advertising module 410 communicates via the central system 418 using the network 416. The advertising module is continuously or periodically updated via the central system to maintain up-to-date linkages between diagnosis and advertising content. This allows smooth, and rapid real-time changes in the linkage between diagnoses and prescription ads which facilitates late-minute and spur-of-the-moment advertising campaigns and rapid modification and fine-tuning of advertising campaigns based on feedback received from the system. In addition, drug information is kept up-to-date from the central system over the network. Prescription writing software system 408 is connected to an output device for the printing of prescription slips and other types of paperwork including receipts and coupons. Prescription writing software system 408 is also connected to the communication module 414 in order to transmit prescription orders over a network such as Internet via e-mail and also via fax and peer-to-peer networking to outside systems such as pharmacies or pharmacy networks or managed care companies or prescription benefit companies.

Figure 5:
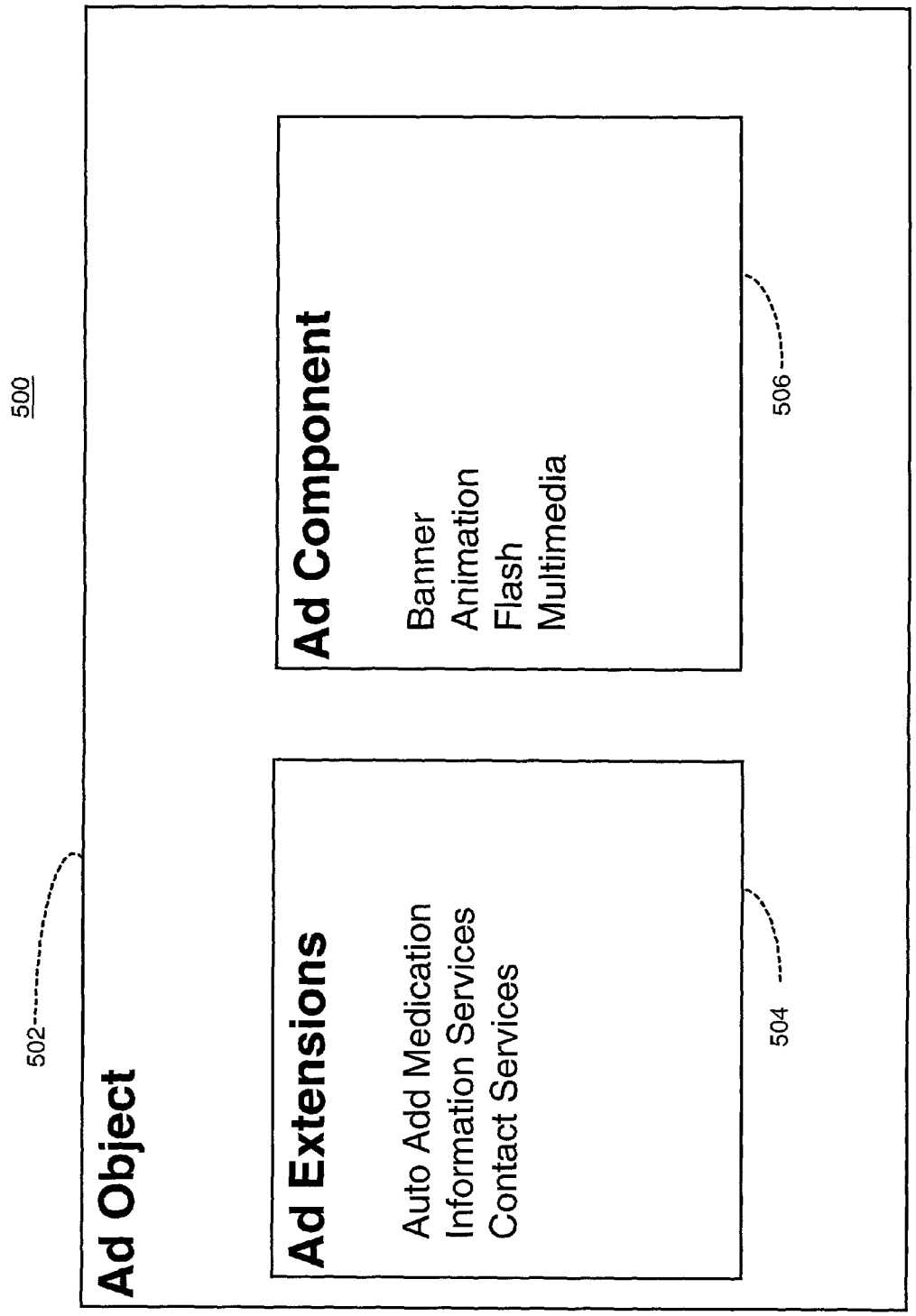
FIG. 5—Depicts the advertising object that resides in the PWSS according to an embodiment of the present invention.

FIG. 5—Advertising Object

FIG. 5 depicts a method 500 according to the present invention. FIG. 5 depicts an advertising object, which is the primary means of displaying advertising content within the medical records software system. Component 502 represents the overall advertising object, which contains advertising component 504 and ad extensions 506. The advertising component represents the advertising itself, which may be a traditional banner ad or animated advertising object such as a Flash object or a variety of multimedia display types. Ad extensions represent enhancements of the advertising component and bring additional functionality and interactive features such as the auto-add function, the information extension, and the contact extension. The auto-add function provides a layer of interaction between the advertising object and the prescription writing software system, the preferred embodiment of which is a prescription list box. The activation of the auto-add function causes the addition of the advertised product data to the prescription writing list box. In the preferred embodiment, a click on the auto-add or "Add-Me" hyperlink or button causes the automatic addition of the advertised prescription to the prescription list box within the medical record software system. The added medication would then be available for immediate selection by a single click on the check box. The auto-add feature would add the default dosage, route, frequency and duration information of the product to the list box. This would enhance the usability in that the user would not have to search for additional prescribing information. However, the user is also able to change easily from the default dose, route, frequency and duration of administration by single clicking on each of these parameters. The "Info" extension provides single click access to additional information services regarding the advertised drugs. In the preferred embodiment, clicking on a hyper-link or button triggers the display of additional pharmaceutical product information in an HTML screen with hyperlinks. The "Contact" extension provides easy access to contact services that allow the user to rapidly contact the product manufacturer or advertiser in order to seek out additional information regarding the product. The contact may be via e-mail, instant messaging technology, live telephonically or via video or other communication methodologies.

FIGS. 6—Interface Screens

Figure 6A:
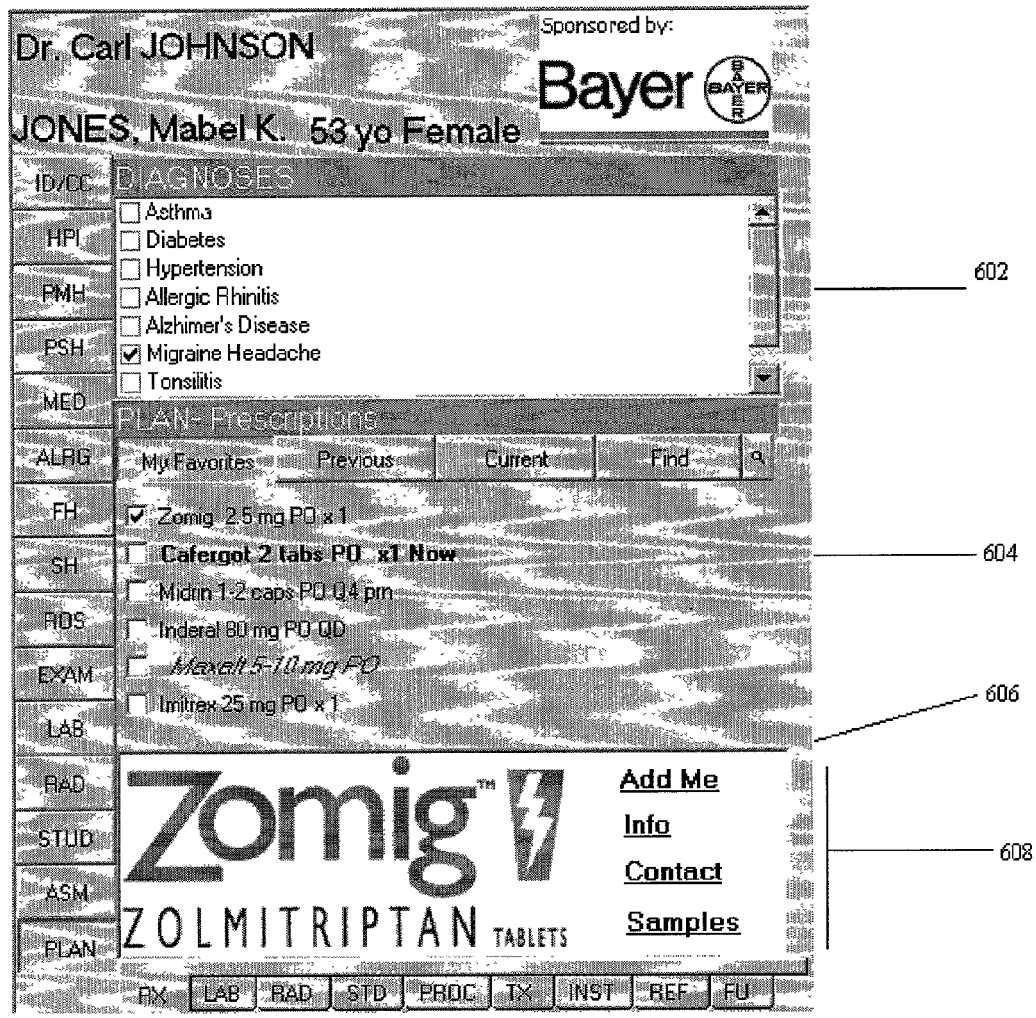
FIGS. 6a and 6b—Depict embodiments of MRSS interface systems with diagnoses being selected and advertisements presented according to an embodiment of the present invention.
Figure 6B:
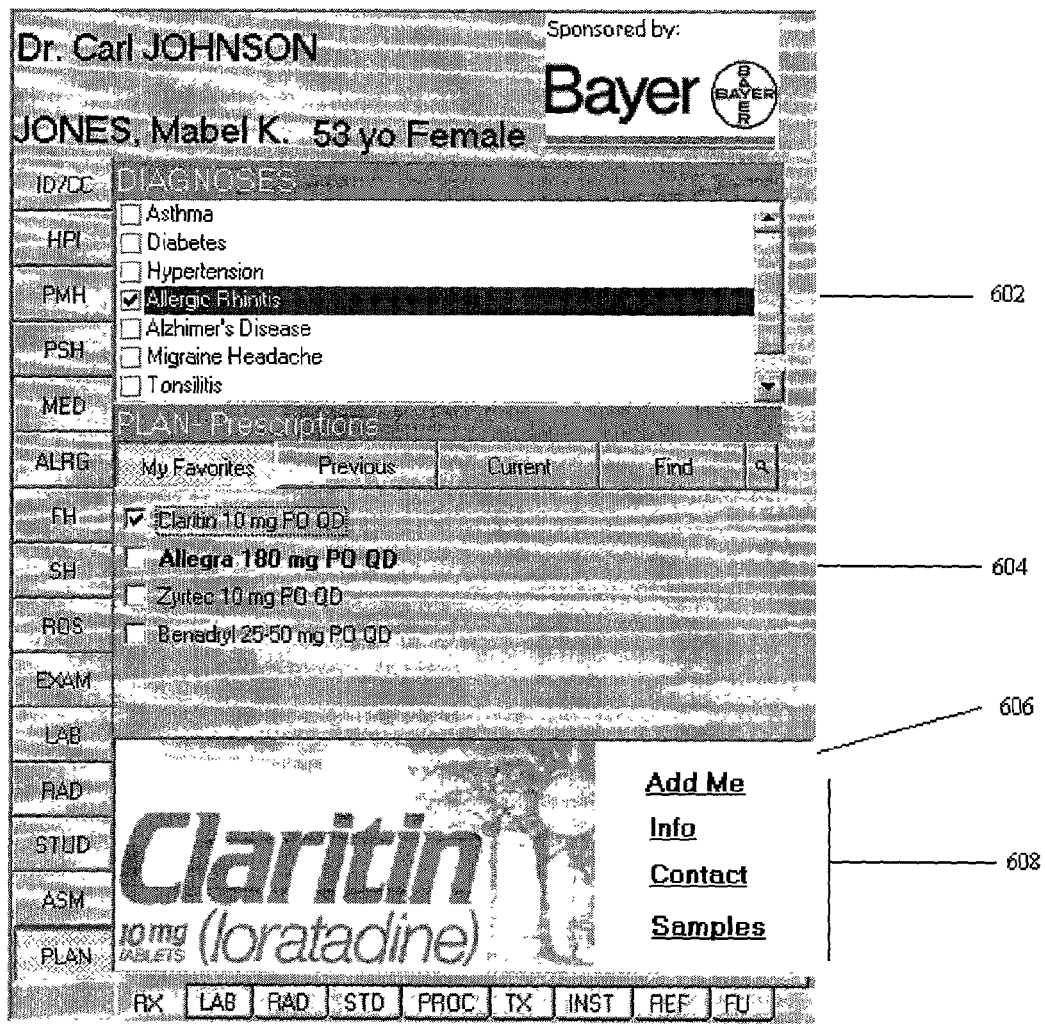

Examples of the interface screen for presentation of the advertisement are presented in FIGS. 6a-6b. In FIG. 6a, a diagnoses section 602, a prescription section 604 and an advertisement system 606 are presented with an advertisement 608 presented therein.

Figure 7:
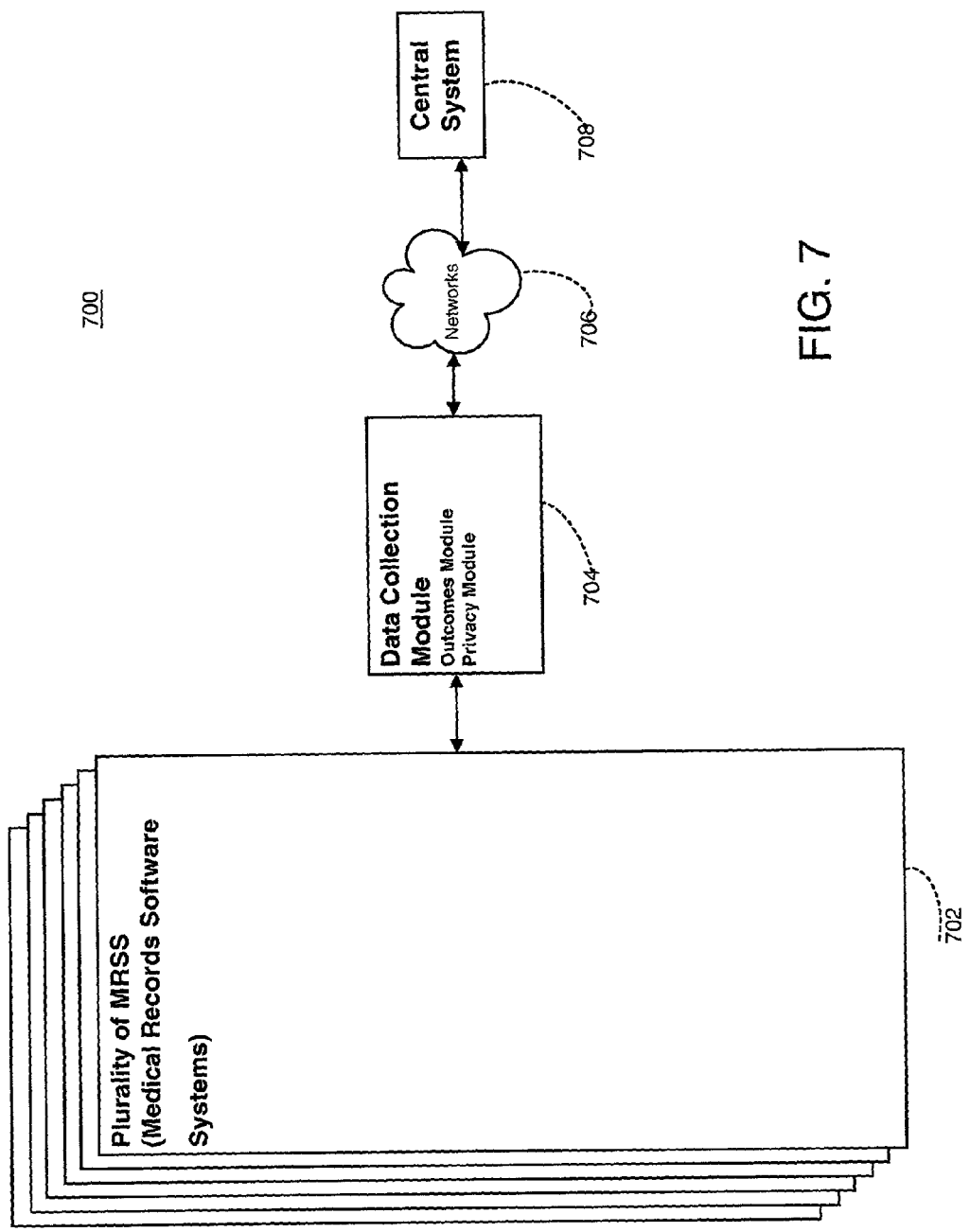
FIG. 7—Depicts a remunerative system for collecting and aggregating clinical information according to an embodiment of the present invention.

FIG. 7—Data Collection

FIG. 7 depicts a method 700 according to the present invention. FIG. 7 depicts a data collection system involving the collection of clinical data from plurality of medical record software systems. Component 702 represents a generic medical record software system. Component 704 represents the data collection module, which contains a module for outcomes analysis of the data provided from the medical record software system as well as the privacy module which is able to extract and exclude a variety of personally identifiable data from the clinical data. The user of the software system is able to interact with the privacy module and control the amount of personal information removed by the privacy module.

Component 706 represents a computer network, the preferred embodiment of which is the Internet. Component 708 represents a central system which collects and analyzes the clinical data from a plurality of medical record software systems. Data collection modules 704 extract data from the medical record software system 702. This has great relevance when applied over large populations for outcome analysis. The privacy module allows the extraction and exclusion of personally identified data in order to annonymize or de-identify the clinically relevant data and protect the patient's confidentiality. The data collection module then communicates with the central system via the network. The central system analyses clinical data from a plurality of software systems, which greatly enhances the relevance of the data.

Figure 8:
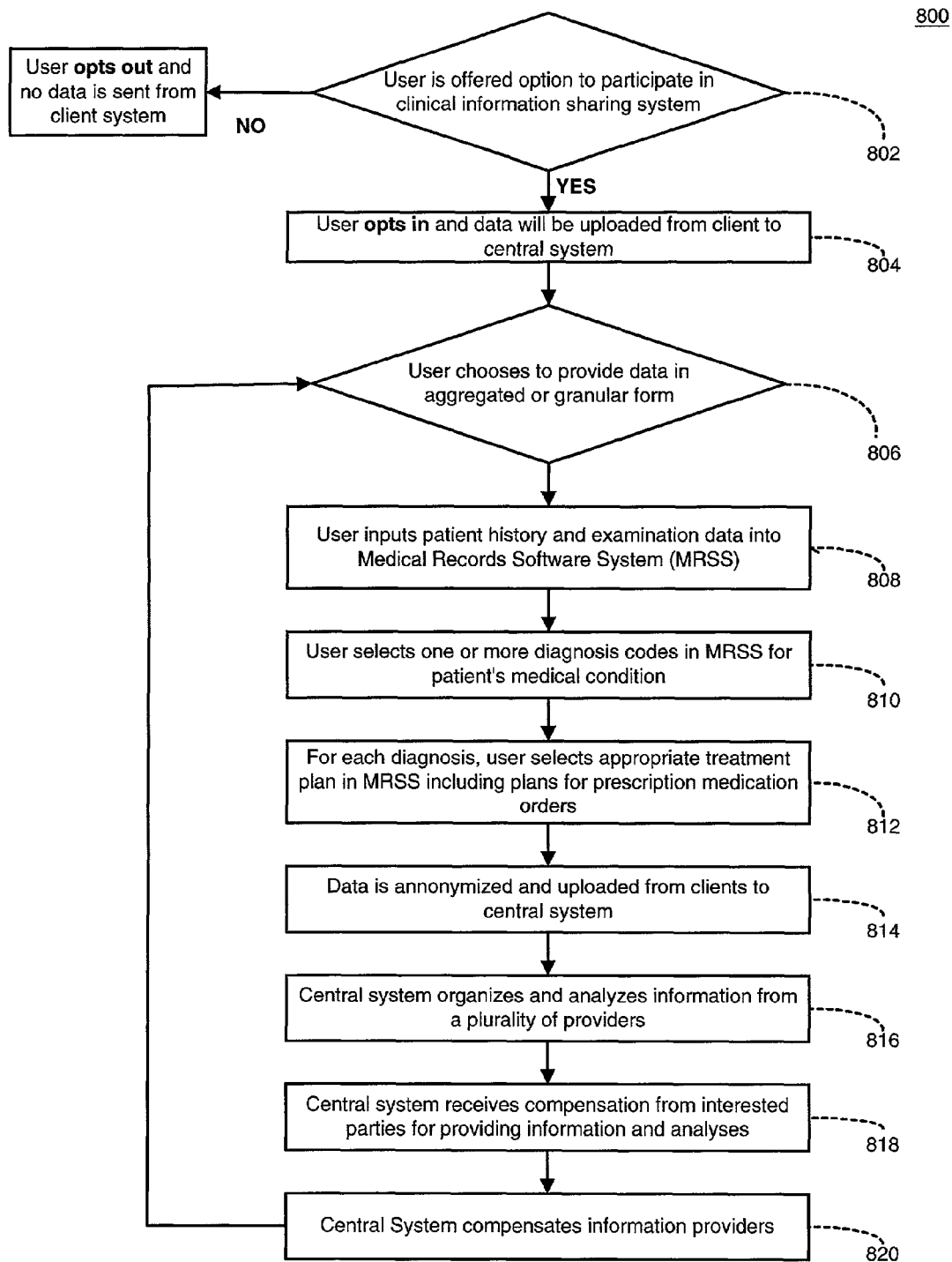
FIG. 8—Depicts a methodology for data collection according to an embodiment of the present invention.

FIG. 8—Data Collection

FIG. 8 is a flow chart of the process of data collection. In step 802, the user in the initial setup sequence is offered the option to participate or not participate in the clinical information sharing system. If the user opts out from the system, then no data of any type is sent from the client system. If the user opts into the system in step 804, this will provide a mechanism for the routine background uploading of clinical information from the client system to the central system. In step 806, the user is offered an option to provide data in either aggregated or more granular form. The user is also offered options to provide data in various levels of anonymization or de-identification. In step 808, the user routinely inputs patient history and examination data into the medical record software system. In step 810, the user selects one or multiple diagnoses within the medical record software system based on the patient's medical condition. In step 812, the user selects an appropriate treatment plan in the medical record software system for each diagnosis or group of related diagnoses. These treatment plans include prescription medication orders selected within the prescription writing software system. In step 814, the data is anonymized to a variable degree and is uploaded from the client to the central system. In step 816, the central system organizes, analyzes and processes the information from a plurality of data providers. In step 818, the central system receives compensation for interested parties for providing information and analyses. In step 820, the central system compensates the data providers.

Figure 9:
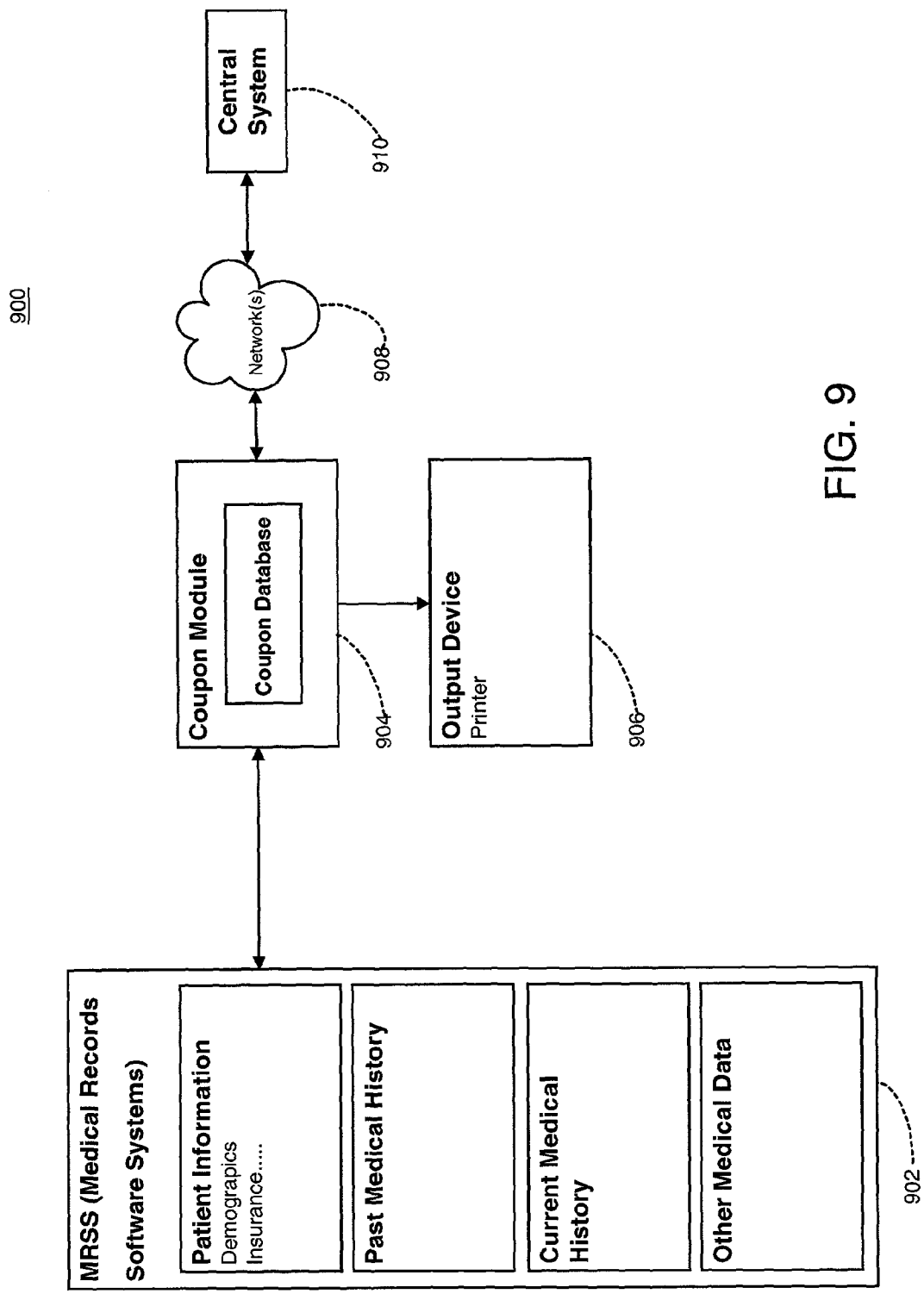
FIG. 9—Depicts a system for issuing coupons as part of a Prescription Writing Software System (PWSS) according to an embodiment of the present invention.

FIG. 9—Coupon System

FIG. 9 depicts a method 900 according to the present invention. FIG. 9 demonstrates a coupon system as a component of the medical record software system. Component 902 represents the Medical Record Software System (MRSS) with sub-components of patient information, past medical history, and current history. Component 904 represents a coupon module of which one component is a coupon database. Component 906 represents an output device, the preferred embodiment of which is a printer and the preferred embodiment of which is a thermal line printer with auto-cut capability similar to that which is seen in a grocery store checkout. Component 908 represents a computer network, the preferred embodiment of which is the Internet. Component 910 represents a central system which organizes and coordinates the coupon system. The coupon module (904) interacts with the medical record software system 902. At the end of a patient encounter, information from the medical record software system is provided to the coupon module and a variety of parameters may be analyzed such as patient demographic information such as age, sex, insurance coverage, and zip code as well as clinical information such as patient's diagnosis, allergies and the medications prescribed at that visit. The coupon module analyzes these parameters and matches them against its coupon database. Coupons, which are relevant to these parameters, are then forwarded to the output device for printing simultaneous to the printing of the patient's prescription slips. The coupon database may reside within the coupon module or on the central system.

Figure 10:
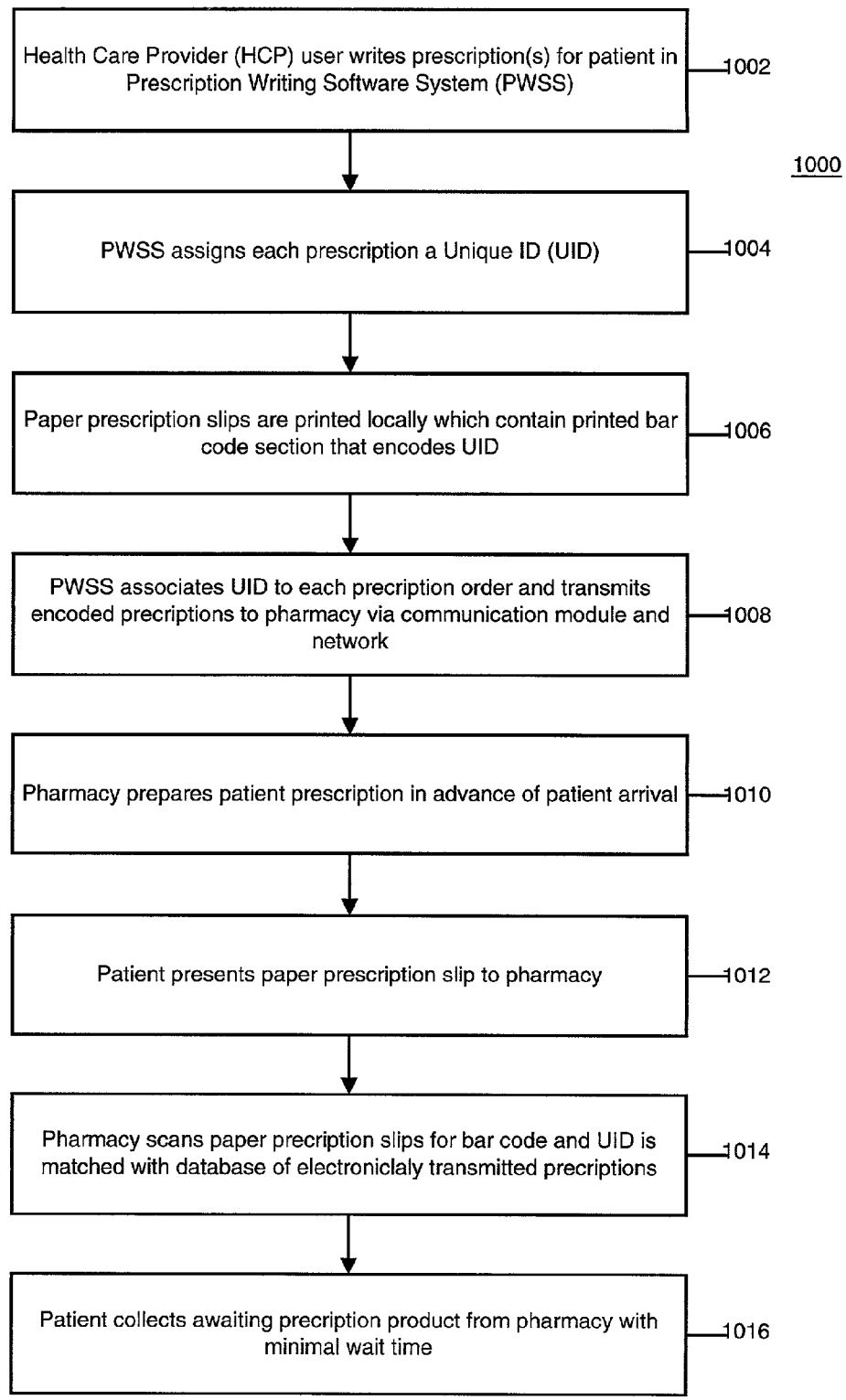
FIG. 10—Depicts a system for allowing bar code tracking of electronically issued prescriptions according to an embodiment of the present invention.

FIG. 10—Bar Code System

FIG. 10 depicts a method 1000 according to the present invention. FIG. 10 depicts a bar code system designed for unique identification of prescriptions over a network coordinated in conjunction with local printing of prescription slips. In step 1002, the health care provider user writes a prescription for patient in the Prescription Writing Software System (PWSS). In step 1004, the PWSS assigns each individual prescription a unique identification number (UID) that contains an encoded ID for the issuing prescriber and for the individual medication. In step 1006, the prescription slips are printed locally on paper with bar code and unique ID recorded on each prescription slip. In step 1008, prescription instruction orders with associated unique IDs are transmitted electronically to the patient's pharmacy and entered into a database.

In step 1010, the pharmacy upon receipt of electronic order prepares the medication order in advance of the patient's arrival. In step 1012, the patient presents their prescription slips to the pharmacy. In step 1014, the pharmacy scans the prescription slip bar codes and matches the prescriptions with records present in their database. One embodiment of a scanner is an optical bar code reader. In another embodiment, the pharmacist visually reads the UID from the paper slip and hand enters the code into the local computer for prescription retrieval. In step 1016, the prescription product is issued to the patient.

Figure 11:
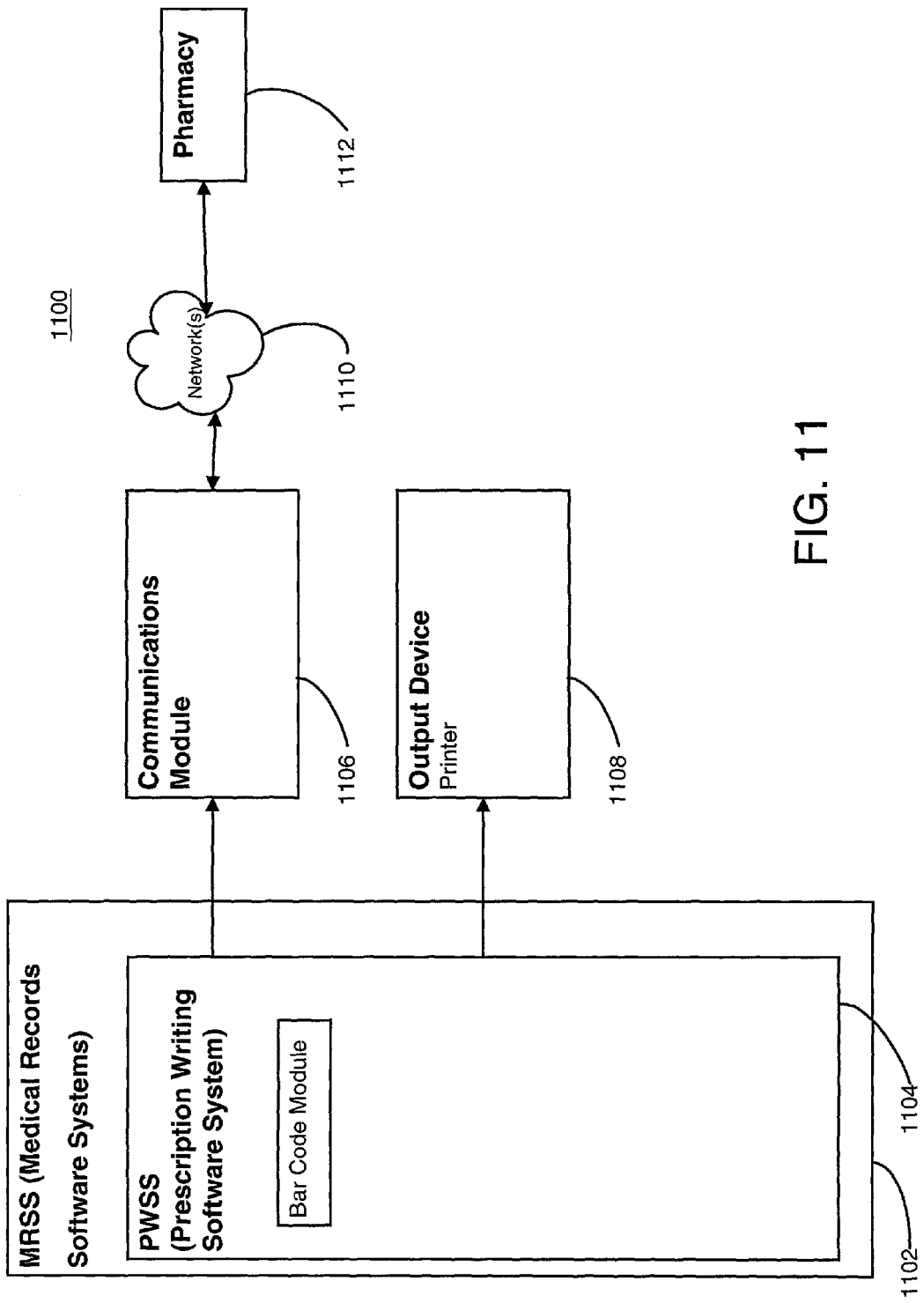
FIG. 11—Depicts the network layout of the bar code tracking system according to an embodiment of the present invention.

FIG. 11—Bar Code System

FIG. 11 depicts a method 1100 according to the present invention. FIG. 11 depicts the system in which bar codes representing unique IDs of a prescription are printed on a paper prescription slip which matches the unique ID transmitted electronically to the patient's pharmacy. This allows the rapid match-up of pre-filled prescription at the pharmacy with the patient's prescription slip. Component 1102 represents a generic medical record software system containing component 1104 which is a prescription writing software system. Component 1106 represents a communication module, which handles communications from the medical record software system. Component 1108 represents an output device, the preferred embodiment of which is a printer, the preferred embodiment of which is a thermal line printer with auto-cut features similar to that seen in a grocery store checkout. Component 1110 represents a network, the preferred embodiment of which is the Internet. Component 1112 represents a pharmacy or pharmacy network, which is connected to a plurality of pharmacies. The pharmacy database may reside locally or remotely such as over a corporate network.

At the end of the patient's office visit, the prescription writing software system component of the medical record software system creates a unique identification number specific to each individual prescription product ordered at that office visit. The series of unique identification numbers with the attached prescription order involving drug name, drug dose, drug frequency, drug route, drug duration and treatment, generic acceptability, number of drug refills, and any other specific prescription information is tagged to the uniquely generated identification number and transmitted to the communications module, from which it is forwarded over the network to the pharmacy system. The same unique identification number is printed either numerically and/or encoded with bar code on the paper prescription slip, which is printed on output device component 1108. The patient then presents the paper prescription slip or receipt to the pharmacy, whereupon the unique identification number is used to retrieve the electronically transmitted records.

Figure 12:
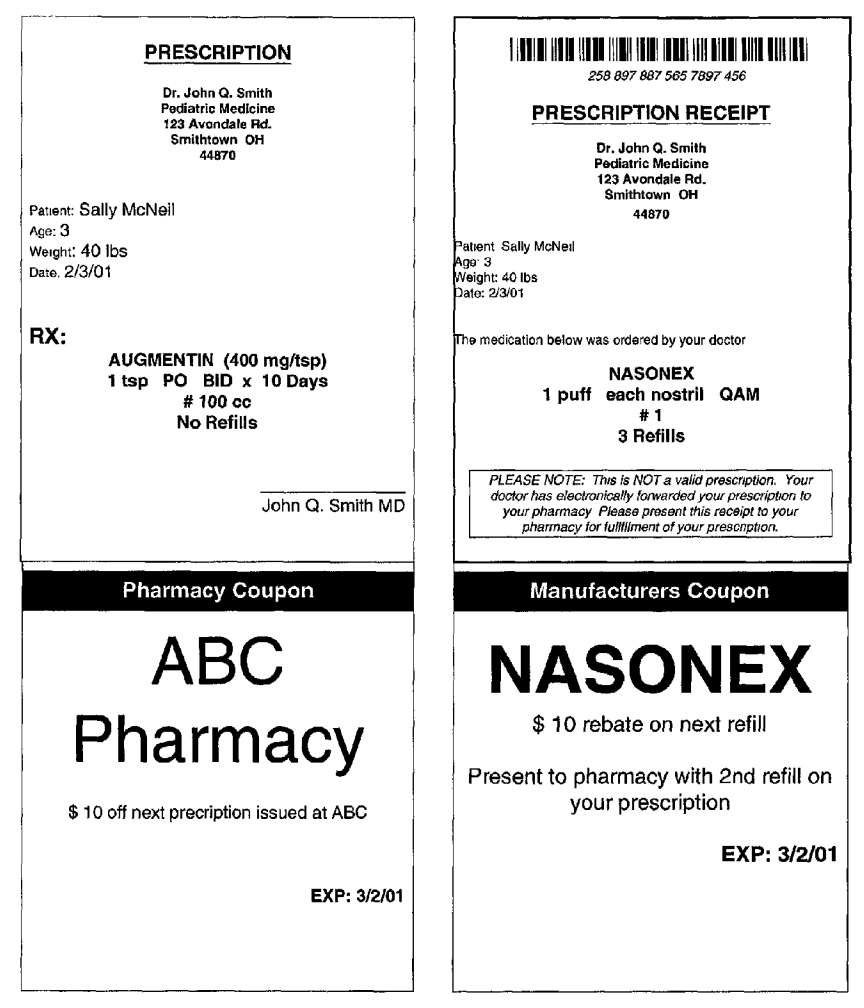

FIG. 12—Bar Coded Prescription and Coupon

FIG. 12 depicts an example of a bar coded prescription and coupon printed from a system of FIG. 11 or any other system according to the present invention.

Although the present invention has been described in terms of various embodiments, it is not intended that the invention be limited to these embodiments. Modification within the spirit of the invention will be apparent to those skilled in the art.

What is claimed is:

1. A computer-implemented method of increasing prescription-issuer awareness of a prescription in a medical records software system that enables a prescription-issuer to input assessments and prescriptions for a patient comprising the steps of:

receiving, at a computer-based system, one or more prescription advertisements from entities responsible for marketing those prescriptions to prescription-issuers;

receiving an agreement to pay for display of the prescription advertisement when a user of the medical records software system selects one or more specific assessments within a group of predetermined assessments;

associating one or more prescriptions with each of a plurality of assessments as being appropriate prescriptions for that assessment in a data storage system associated with the computer-based system;

associating the one or more prescription advertisements with the one or more specific assessments for which payment has been agreed in a data storage system associated with the computer-based system;

receiving a prescription-issuer selection of an assessment from a group of possible assessments presented to the prescription issuer;

upon receiving selection of an assessment, presenting appropriate prescriptions associated with the assessment selected on a display device; and upon receiving a selection of a specific assessment for which payment has been agreed, in addition to presenting appropriate prescriptions, presenting at least one prescription advertisement selected from the one or more prescription advertisements associated with the specific assessment as being prescription advertisements for which an entity has agreed to pay for the specific assessment selected in the medical records software system to the prescription-issuer on the display device.

2. The method of claim 1 wherein a plurality of prescriptions may correspond to a single assessment.

3. The method of claim 1 wherein each prescription advertisement may correspond to a plurality of assessments.

4. The method of claim 1 wherein one or more combinations of assessments may correspond to a single prescription advertisement.

5. The method of claim 1 wherein the association between assessments and prescription advertisements is dynamic.

6. The method of claim 5 further comprising the step of updating the association over a computer network from a central server system.

7. The method of claim 5 wherein the association is dynamically changed by a time schedule.

8. The method of claim 7 wherein the association is rotated according to a predetermined schedule.

9. The method of claim 1 wherein the prescription advertisement is presented in a prescription writing portion of a graphical user interface.

10. The method of claim 1 wherein the prescription advertisement is presented in any portion of the graphical user interface of the medical records software system.

11. The method of claim 1 wherein the prescription advertisement comprises a banner advertisement in the graphical user interface of the prescription issuing system.

12. The method of claim 1 wherein the prescription advertisement comprises visual differentiation of the prescription in a list of available prescriptions.

13. The method of claim 1 further comprising adding the prescription associated with the prescription advertisement as a default prescription for the at least one assessment.

14. The method of claim 13 further comprising the step of charging an entity responsible for marketing the prescription for placement of the advertisement in the prescription issuing system.

15. The method of claim 1 further comprising the step of presenting extensions of the prescription advertisement that provide additional information.

16. The method of claim 15 further wherein the extension comprises an onscreen display of product information related to the prescription advertised.

17. The method of claim 15 wherein the extension initiates a connection for the prescription-issuer electronically to an Internet site with information about the prescription.

18. The method of claim 15 wherein the extension initiates a connection for the user telephonically to a live customer service representative.

19. The method of claim 15 wherein the extension initiates a connection for the user via electronic mail to a representative of the prescription advertised.

20. The method of claim 15 wherein the extension initiates a connection for the user via instant messaging to a representative of the prescription advertised.

21. The method of claim 15 wherein the extension initiates a connection for the user to a companion Internet site associated with the prescription advertised.

22. The method of claim 15 wherein the extension initiates a request to send samples of the prescription to the prescription-issuer.

23. The method of claim 15 wherein the extension initiates an interface through which the provider may sign up to participate in the clinical study.

24. The method of claim 23 wherein information related to the clinical study are forwarded to the advertiser in return for the contact with the participant.

25. The method of claim 1 further comprising the step of recording user interactions with prescription advertisements.

26. The method of claim 23 further comprising the step of transmitting advertisement activity recorded to a central system.

27. The method of claim 23 further comprising the step of transmitting click through rates to the advertisers.

28. The method of claim 23 further comprising the step of transmitting response rates of prescriptions of the advertised prescription.

29. The method of claim 1 further comprising the step of compensating an entity responsible for the content of the prescription issuing system for placement of the advertisement in the prescription issuing system.

30. The method of claim 1 further comprising:
   determining demographic information from the medical records software system related to one or more members of a particular prescription-issuer/prescription recipient interaction; and
   presenting a prescription advertisement for the prescription in the medical records software system interface to the prescription-issuer based on a determination of a correspondence between the demographic information of a target audience for the prescription advertisement and the demographic information of the particular prescription-issuer/prescription recipient interaction.

31. The method of claim 30 wherein the demographic information relates to the patient.

32. The method of claim 30 wherein the demographic information relates to the physician using the medical records software system.

33. A computer-based system for issuing prescriptions comprising a plurality of modules operating on one or more computer devices, the modules comprising:
   an advertising module that receives prescription advertisements from entities responsible for marketing the prescriptions to prescription-issuers and a promise to pay a specific amount for display of the prescription advertisement upon selection of a specific assessment for patients by the prescription issuer in a prescription issuing software system;
   a diagnosis module that presents a graphical user interface on a display through which a health care provider may input one or more assessments for a patient;
   a planning module that presents a graphical user interface on a system that includes a display and at least one input mechanism through which a health care provider inputs one or more prescriptions for a selected assessment or group of assessments; and
   a prescription advertising display module that presents an advertisement on a display device for a prescription assigned to the selected assessment or group of assessments because the assessment was selected and the advertisement relates to a prescription assigned to the selected assessment.

34. The system of claim 33 wherein the advertising module controls the advertisements presented by prescription advertising module by updating the assignment of prescriptions to be advertised with assessments for which those advertisements are made.

35. The system of claim 34 wherein the advertising system connects to a plurality of prescription advertising modules over a network.

36. The system of claim 33 further comprising an advertising database that stores advertisements to be presented.

37. The system of claim 36 wherein the advertisement database is connected to the medical record system over the Internet.

38. The system of claim 33 wherein the relationship between prescription advertisements and assessments may include one to one, one to many, and many to one.

39. A computer-based method of delivering prescription data comprising the steps of:
   storing assessment and prescription information issued by prescription-issuers using a plurality of prescription issuing systems in at least one data storage device, each prescription issuing system comprising at least one computer-based system;
   through a graphical interface presented by the computer-based system, offering an option through the prescription issuing system to participate in centralized data collection of assessment/prescription information from a plurality of prescription-issuers; and
   if the option is accepted, electronically transmitting data stored in the prescription issuing system over a network connection to one or more third party computer-based systems connected to that network, wherein the one or more third party computer-based systems aggregate assessment/prescription information from a plurality of prescription-issuers.

40. The method of claim 39 wherein the user that accepted the option to participate is compensated from one or more third parties to the central system for receipt of the assessment and prescription information.

41. The method of claim 39 further comprising the step of coupling prescription information and patient data.

42. The method of claim 41 further comprising the step of transmitting prescription information and patient data to the one or more third parties.

43. The method of claim 42 wherein the one or more third parties comprise a central computer system.

44. The method of claim 39 wherein the one or more third parties comprise a central computer system.

45. The method of claim 44 wherein the central computer system aggregates data from a plurality of users.

46. The method of claim 39 further comprising the step of transmitting clinical outcome data.

47. The method of claim 46 wherein the one or more third parties comprise a central computer system.

48. The method of claim 47 wherein the central computer system aggregates data from a plurality of users.

49. The method of claim 48 wherein the central computer system operator is compensated for providing data to interested parties.

50. The method of claim 46 further comprising the step of cleansing the patient data prior to transmission to comply with one or more privacy requirements.

51. The method of claim 39 further comprising the step of distributing revenue generated from distribution of the assessment and prescription information between the health care providers, the prescription issuing system distributors, the central system, agents for the central system, assessment/prescription collection entities, data analysis entities, and prescription entities.

* * * * *